United States Patent
Kim et al.

(10) Patent No.: US 10,064,865 B2
(45) Date of Patent: Sep. 4, 2018

(54) COMPOSITION COMPRISING PHOSPHODIESTERASE TYPE 5 INHIBITOR FOR INHIBITING APOPTOSIS OF NERVE CELLS

(71) Applicants: ARIBIO INC., Seoul (KR); SK CHEMICALS CO., LTD., Seongnam-Si (KR)

(72) Inventors: Myung Hwa Kim, Yongin-Si (KR); Jae Jun Choung, Yongin-Si (KR); Sae Kwang Ku, Daegu (KR)

(73) Assignees: ARIBIO CO., LTD., Sungnam, Gyeonggi-Do (KR); SK CHEMICALS CO., LTD., Seongnam-Si (KR)

( * ) Notice: Subject to any disclaimer, the term of this patent is extended or adjusted under 35 U.S.C. 154(b) by 0 days.

(21) Appl. No.: 15/663,092

(22) Filed: Jul. 28, 2017

(65) Prior Publication Data

US 2017/0326145 A1 Nov. 16, 2017

Related U.S. Application Data

(63) Continuation of application No. 14/649,467, filed as application No. PCT/KR2013/011180 on Dec. 4, 2013, now Pat. No. 9,750,743.

(30) Foreign Application Priority Data

Dec. 4, 2012 (KR) .................. 10-2012-0139594

(51) Int. Cl.
| | |
|---|---|
| *A61K 31/4745* | (2006.01) |
| *A61K 31/495* | (2006.01) |
| *A61K 31/4985* | (2006.01) |
| *A61K 31/505* | (2006.01) |
| *A61K 31/519* | (2006.01) |
| *A61K 31/53* | (2006.01) |
| *A61K 31/00* | (2006.01) |

(52) U.S. Cl.
CPC ............ *A61K 31/519* (2013.01); *A61K 31/00* (2013.01); *A61K 31/4985* (2013.01); *A61K 31/53* (2013.01); *A61K 31/4745* (2013.01); *A61K 31/495* (2013.01); *A61K 31/505* (2013.01)

(58) Field of Classification Search
CPC .............. A61K 31/495; A61K 31/4745; A61K 31/4985; A61K 31/505; A61K 31/519
USPC ............................ 514/252.16, 249, 250, 292
See application file for complete search history.

(56) References Cited

U.S. PATENT DOCUMENTS

2005/0107405 A1 5/2005 Takasaka

FOREIGN PATENT DOCUMENTS

| EP | 2535049 A1 | 12/2012 | |
|---|---|---|---|
| KR | 1020010031944 A | 4/2001 | |
| KR | 1020060031614 A | 12/2006 | |
| WO | 0132170 A1 | 5/2001 | |
| WO | WO-2006091542 A2 * | 8/2006 | ............. A61K 31/22 |

OTHER PUBLICATIONS

Ko et al., "Tadalafil improves short-term memory by suppressing ischemia-induced apoptosis of hippocampal neuronal cells in gerbils", Pharmacology, Biochemistry and Behavior, vol. 91, No. 4, pp. 629-635 (Feb. 2009).
Caretti et al., "Phosphodiesterase-5 Inhibition Abolishes Neuron Apoptosis Induced by Chronic Hypoxia Independently of Hypoxia-Inducible Factor-1a Signaling", Experimental Biology and Medicine, vol. 233, No. 10, pp. 1222-1230 (2008).
Boess et al., "Inhibition of phosphodiesterase 2 increases neuronal cGMP, synaptic plasticity and memory performance," Neuropharmacology, vol. 47, No. 7, pp. 1081-1092 (2004).
Chen et al., "Induction of caspase-3-like protease may mediate delayed neuronal death in the hippocampus after transient cerebral ischemia," J Neurosci, vol. 18, No. 13, pp. 4914-4928 (1998).
Sarafti et al., "Sildenafil and vardenafil, types 5 and 6 phosphodiesterase inhibitors, induce caspase-dependent apoptosis of B-chronic lymphocytic leukemia celis," Blood, vol. 101, No. 1, pp. 265-269 (2003).
International Search Report and Written Opinion for International Application No. PCT/KR2013/011180, dated Apr. 21, 2014 (13 pages).
European Search Report for corresponding European Application No. EP13860159, dated Aug. 12, 2015 (3 Pages).
European Office Action for corresponding European Application No. EP13860159, dated Oct. 21, 2015 (3 Pages).

* cited by examiner

*Primary Examiner* — Kevin E Weddington
(74) *Attorney, Agent, or Firm* — Lucas & Mercanti, LLP

(57) ABSTRACT

The present invention relates to a composition and health functional food for inhibiting apoptosis of cranial nerve cells, and to a method for inhibiting apoptosis, wherein the composition and health functional food comprising a phosphodiesterase type 5 active inhibitor. According to the present invention, the PDE5 inhibitor exhibits a protective effect on nerve cells by inhibiting apoptosis of cranial nerve cells. Thus, the present invention can be effectively used to prevent, alleviate, and treat cranial nerve disease.

9 Claims, 8 Drawing Sheets

COMPOSITION COMPRISING PHOSPHODIESTERASE TYPE 5 INHIBITOR FOR INHIBITING APOPTOSIS OF NERVE CELLS

CROSS-REFERENCE TO RELATED APPLICATION

This application is a continuation of U.S. patent application Ser. No. 14/649,467, filed Jun. 3, 2015, which is a 371 National Phase Entry Application of PCT/KR2013/011180 filed Dec. 4, 2013, which claims the benefit of Korean Patent Application No. 10-2012-0139594 filed Dec. 4, 2012, the contents of each of which are incorporated herein by reference.

FIELD OF THE INVENTION

The present invention relates to a composition and functional health food containing a phosphodiesterase type 5 inhibitor for inhibiting brain neuron apoptosis and a method for inhibiting apoptosis.

BACKGROUND OF THE INVENTION

Phosphodiesterase (PDE) is an enzyme that catalyzes the hydrolysis of cyclic AMP and/or cyclic GMP into 5-AMP and 5-GMP, respectively, in cells, and thus this enzyme is important in the cellular regulation at the level of cAMP or cGMP. So far, 11 families of PDEs have been known (Nature, 674-682(2002)). Of the PDEs, PDE 5 is an enzyme that decomposes cGMP to generate 5'-GMP, and thus it has been reported that the inhibition of PDE 5 maintains the concentration of cGMP to make an erection last (Boolel, M. et al., Br. J. of Urology, 78, 257-261(1996)). Therefore, a PDE 5 inhibitor is used as an erectile dysfunction medication.

Many compounds are known as a PDE 5 inhibitor. Viagra™ (generic name: sildenafil; WO 94/28902) was approved as the first male erectile dysfunction medicine by the U.S. FDA, and Cialis™ (generic name: tadalafil; WO 95/19978) and Levitra™ (generic name: vardenafil; Bioorganic & Medicinal Chemistry Letters) were permitted. Embix™ (generic name: mirodenafil; KR0358083) is also known as a PDE 5 inhibitor. The above medications are known to show an excellent treatment effect and thus improve the sexual function in approximately 70% of patients. As other medicinal uses of the PDE 5 inhibitor, the treatment effects of portal hypertension, liver-kidney syndrome, and liver-lung syndrome are known (Korean Patent Publication No. 10-2012-0024807), and the improvement effect of a reproductive capacity of mammals has also been reported (Korean Patent Publication No. 10-2002-0031062).

In addition, it has been reported that sildenafil and vardenafil as PDE 5 inhibitors induce caspase-dependent apoptosis of B-chronic lymphocytic leukemia cells (Marika Sarfati et al., BLOOD, VOLUME 101, NUMBER 1(2003)).

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

While researching PDE 5 inhibitors, the present inventors have found that the PDE 5 inhibitor rather inhibits neuron apoptosis in the brain. Specifically, the present inventors have confirmed that, as a result of administering a PDE 5 inhibitor to an animal model with induced neuron apoptosis due to a brain injury, the brain neuron apoptosis was significantly inhibited, and the deteriorations in cognitive and motor functions of the animal model were improved by a neuroprotective effect through neuron apoptosis, and then have completed the present invention.

Therefore, the present invention has been made in view of the above-mentioned problems, and an aspect of the present invention is to provide a pharmaceutical composition for inhibiting brain neuron apoptosis.

Another aspect of the present invention is to provide a functional health food for inhibiting brain neuron apoptosis.

Still another aspect of the present invention is to provide a method for inhibiting brain neuron apoptosis.

Other objects and advantages of the present invention will become apparent from the detailed description to follow taken in conjunction with the appended claims and drawings.

The features and advantages of this invention will be summarized as follows:

(i) The present invention provides a composition and functional health food containing a PDE 5 inhibitor for inhibiting brain neuron apoptosis and a method for inhibiting apoptosis.

(ii) According to the present invention, the PDE 5 inhibitor exhibits a neuroprotective function by inhibiting brain neuron apoptosis.

(iii) The composition of the present invention can prevent, ameliorate, and treat brain nerve disease through the inhibition of apoptosis of brain nerve cells.

$^a$p<0.01 as compared with sham control by LSD test,
$^b$p<0.01 as compared with neuron apoptosis control by LSD test,
$^c$p<0.01 as compared with sham control by MW test.

Figure 6:
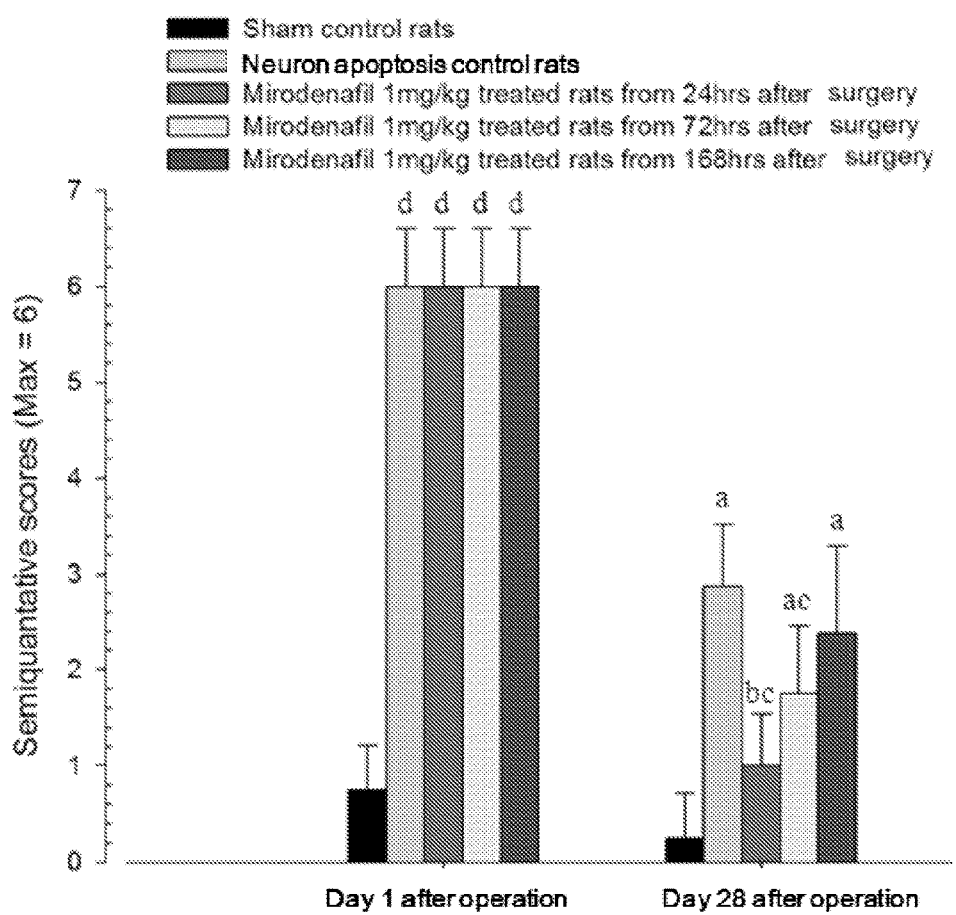

FIG. 6 shows the change in the hindlimb placing test score according to the timing of mirodenafil treatment.

$^a$p<0.01 and $^b$p<0.05 as compared with sham control by LSD test,
$^c$p<0.01 as compared with neuron apoptosis control by LSD test,
$^d$p<0.01 as compared with sham control by MW test.

Figure 7:
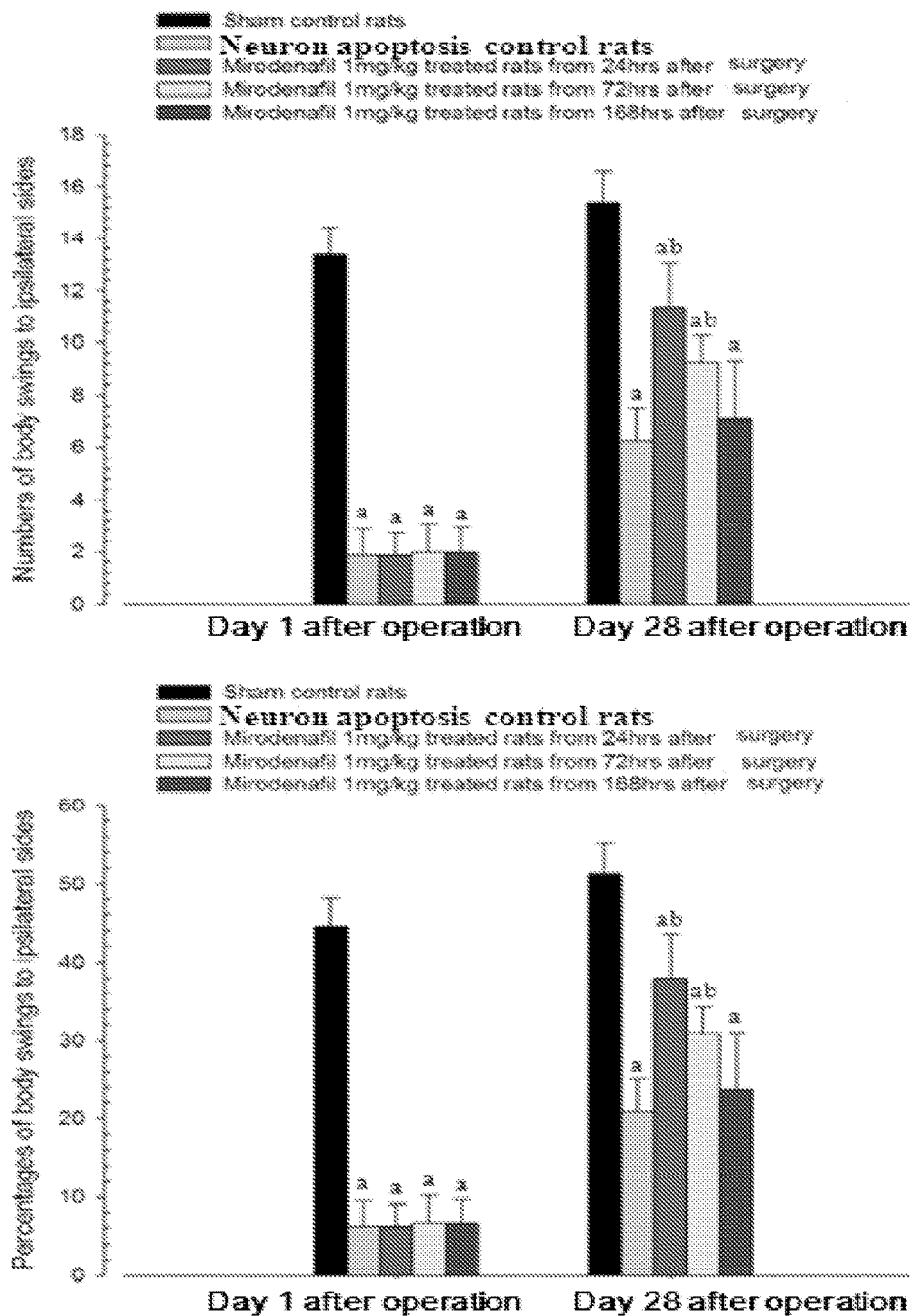

FIG. 7 shows the change in the body swing according to the timing of mirodenafil treatment. Values are expressed as Mean±SD of eight rats.

$^a$p<0.01 as compared with sham control by LSD test,
$^b$p<0.01 as compared with neuron apoptosis control by LSD test.

Figure 8:
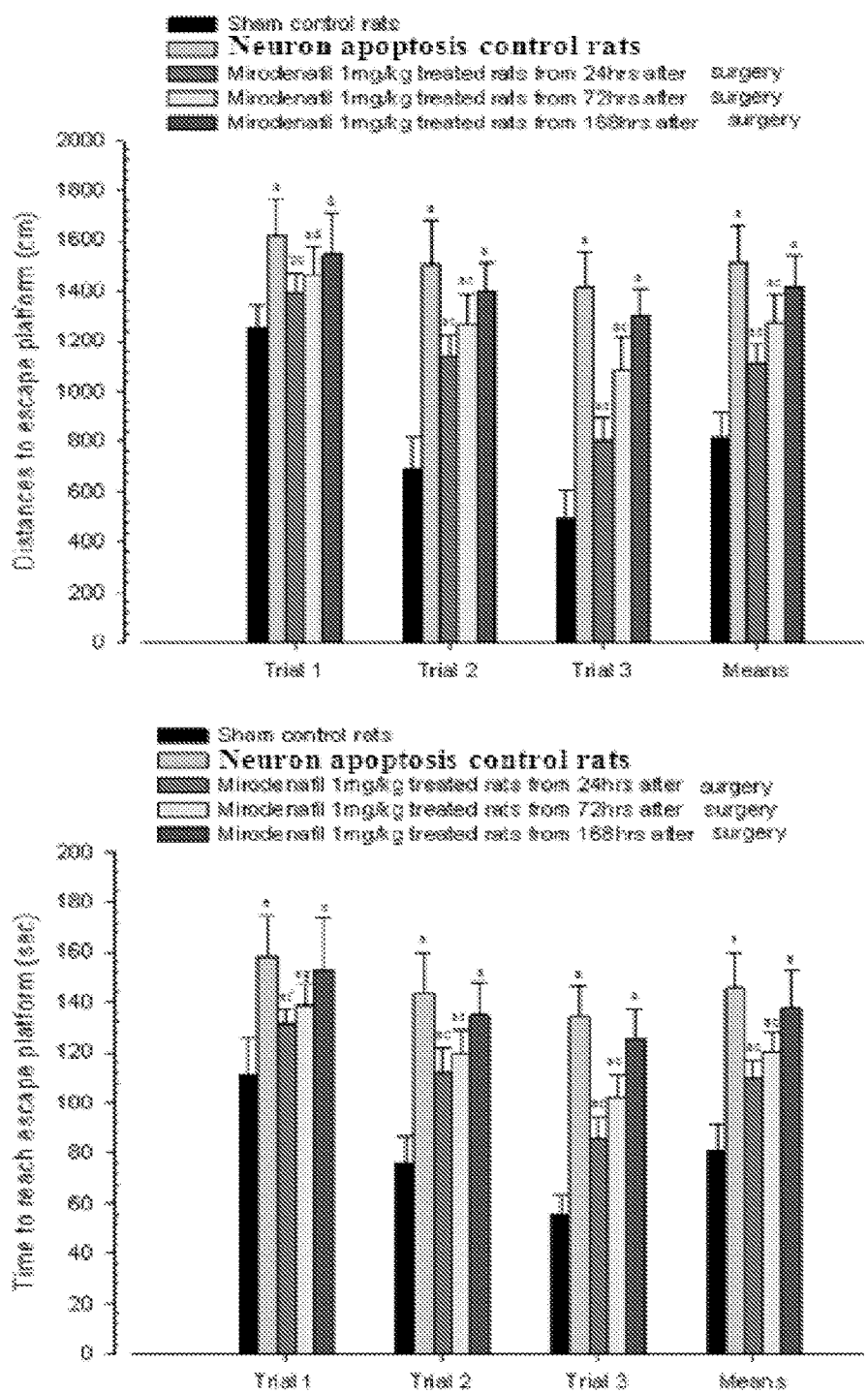

FIG. 8 shows the change in cognitive motor behavior (water tank task) according to the timing of mirodenafil treatment. Values are expressed as Mean±SD of eight rats.

$^a$p<0.01 and $^b$p<0.05 as compared with sham control by LSD test,
$^c$p<0.01 and $^d$p<0.05 as compared with neuron apoptosis control by LSD test,
$^e$p<0.01 as compared with sham control by LSD test,
$^f$p<0.01 and $^g$p<0.05 as compared with neuron apoptosis control by LSD test.

DETAILED DESCRIPTION OF THE INVENTION

In accordance with an aspect of the present invention, there is provided a pharmaceutical composition for inhibiting brain neuron apoptosis, comprising: (i) a pharmaceutically effective amount of phosphodiesterase type 5 inhibitor; and (ii) a pharmaceutically acceptable carrier.

In accordance with another aspect of the present invention, there is provided a method for inhibiting brain neuron apoptosis in a subject in need thereof, comprising administering a composition containing a phosphodiesterase type 5 inhibitor in an effective amount to the subject.

In accordance with still another aspect of the present invention, there is provided a method for improving cognitive dysfunction and motor dysfunction in a subject in need thereof, comprising administering a composition containing a phosphodiesterase type 5 inhibitor in an effective amount to the subject.

While researching PDE 5 inhibitors, the present inventors have found that the PDE 5 inhibitor rather inhibits brain neuron apoptosis. Specifically, the present inventors have confirmed that, as a result of administering a PDE 5 inhibitor to an animal model with induced neuron apoptosis due to a brain injury, the brain neuron apoptosis was significantly inhibited, and the deteriorations in cognitive and motor functions of the animal model were improved by a neuroprotective effect through brain neuron apoptosis inhibition.

As used herein, the term "phosphodiesterase type 5 inhibitor" or "PDE 5 inhibitor" refers to a material that can selectively or non-selectively inhibit or reduce the catalytic function of PDE 5. The PDE 5 inhibitor includes a compound, a peptide, a small molecule, an antibody or a fragment thereof, and a natural extract.

In one particular embodiment, the PDE 5 inhibitor is a compound.

According to one embodiment of the present invention, the PDE 5 inhibitor is selected from the group consisting of mirodenafil, sildenafil, vardenafil, tadalafil, udenafil, dasantafil, and avanafil; and a pharmaceutically acceptable salt, solvate, and hydrate thereof.

In one particular embodiment, the PDE 5 inhibitor is mirodenafil, sildenafil, vardenafil, or a pharmaceutically acceptable salt thereof.

The term "pharmaceutically acceptable salt" refers to a formulation of a compound that does not cause significant irritation to an organism to which it is administered and does not abrogate the biological activity and properties of the compound. The pharmaceutically acceptable salt can be obtained by allowing the compound of the present invention to react with inorganic acids such as hydrochloric acid, bromic acid, sulfuric acid, nitric acid, phosphoric acid; sulfonic acids such as methanesulfonic acid, ethanesulfonic acid, and p-toluenesulfonic acid; or organic carbonic acids such as tartaric acid, formic acid, citric acid, acetic acid, trichloroacetic acid, trifluoroacetic acid, capric acid, isobutene acid, malonic acid, succinic acid, phthalic acid, gluconic acid, benzoic acid, lactic acid, fumaric acid, maleic acid and salicylic acid; hydrobromic acid and hydroiodic acid. Also, the salts may be obtained by allowing the compound of the present invention with bases to form with alkali metal bases such as ammonium salt, sodium salt or potassium salt; alkaline earth metal bases such as calcium salt and magnesium salt; salts with organic bases such as dicyclohexylamine, N-methyl-D-glucamine and tris(hydroxymethyl)methylamine; or salts with amino acids such as arginine and lysine.

According to one embodiment, the pharmaceutical acceptable salt is mirodenafil hydrochloride, sildenafil citrate, or vardenafil hydrochloride.

The hydrate is the stoichiometry (stoichiometric) or non-stoichiometric (non-stoichiometric) the compounds of the present invention, which contains water in the amount of binding by non-covalent intermolecular forces (non-covalent intermolecular force) or it means a salt thereof.

The solvate means a compound or its salt of the present invention, which contains the solvent in a stoichiometric or non-stoichiometric combined by non-covalent intermolecular forces. Preferred solvents include volatile solvents are suitable for non-toxic, and/or administered to a human thereof.

As provided in examples below, the composition of the present invention containing the PDE 5 inhibitor as an active ingredient inhibits brain neuron apoptosis to protect neurons. As used herein, the term "neurons" includes neurons, neural support cells, glia, Schumann cells, and the like, which constitute structures of the central nerve system, brain, brain stem, spinal cord, and junction portions of the central nerve system and the peripheral nervous system, and the like. As used herein, the term "neuroprotective" refers to an action of reducing or ameliorating nervous insult, an action of reducing or inhibiting neuron apoptosis by nervous insult, or an action of protecting or restoring neurons suffering nervous insult. In addition, as used herein, the term "nervous insult" refers to damage of neurons or nerve tissues, resulting from various causes (e.g.: external factors such as traumatic brain injury, genetic causes, metabolic causes, toxic causes, neurotoxic causes, physiological cause, biochemical causes, and the like).

According to an embodiment of the present invention, the composition can be applied to the prevention or treatment of brain nerve disease. As used herein, the term "prevention" refers to reducing the probability/risk of brain nerve disease in a subject, delaying the occurrence of brain nerve disease in a subject, or a combination thereof. As used herein, the term "treatment" refers to inhibiting the development of brain nerve disease occurring in a subject, reducing (ameliorating) the symptoms of brain nerve disease occurring in a subject, removing brain nerve disease occurring in a subject, or a combination thereof. As used herein, the term "amelioration" is used in the same meaning as the term "treatment". The term "subject" that is prevented or treated by the pharmaceutical composition of the present invention refers to a human or a non-human animal, and preferably refers to a human According to an embodiment of the present invention, the brain nerve disease is selected from the group consisting of neuronal degenerative disease, ischemic stroke, cognitive dysfunction, and motor dysfunction.

The neuronal degenerative disease that is prevented or treated by the composition of the present invention includes dementia, Huntington's disease, Parkinson's disease, and amyotrophic lateral sclerosis. The dementia includes AIDS-induced dementia, Lewy body dementia, frontotemporal dementia, multi-infarct dementia, semantic dementia, Alzheimer's dementia, and vascular dementia.

The cognitive dysfunction that is prevented or treated by the composition of the present invention includes memory loss, learning disability, agnosia, amnesia, aphasia, apraxia, and delirium.

The motor dysfunction that is prevented or treated by the composition of the present invention includes motor disturbance, paralysis, ataxia, dyskinesia, spasticity, and dystonia. The motor disturbance means a state in which the body volitional movement, for example, the movements of the limbs, trunk, neck, face, face, tongue, and the like are not voluntary. The paralysis is a dysfunction of the nerve or muscle without changing shapes thereof, and means the loss of sensation or an immobile state. Paralysis may be divided into motor paralysis, which has an immobile state as the main symptom, and sensory paralysis, in which sensation is lost, depending on the symptom, and includes monoplegia, hemiparalysis, paraplegia, and quadriplegia.

The ataxia means a state in which, even though the muscular power is normally maintained, the intercooperation between muscle groups involved in the movement is not maintained and smooth movement is disturbed. The dyskinesia means a phenomenon in which voluntary movement is reduced and involuntary movement (tic disorder or choreic movement) is shown. The spasticity means muscle tension that increases in proportion to the rate of muscle stretching (increasing) due to hyperexcitation of stretch reflex. Here, the stretch reflex refers to a phenomenon in which, when the skeletal muscle continuously stretches, the stretched muscle reflexively contracts as if the muscle resists the stretching, and thus the tension increases. The dystonia means a generic term for symptoms, such as twisting of a part of the body, repeated movements, or abnormal postures, due to the continuous muscular contraction.

According to an embodiment of the present invention, the composition of the present invention can inhibit brain neuron apoptosis caused by a traumatic brain injury. Accordingly, the composition of the present invention can be used to ameliorate neurological and cognitive motor behavior disorders caused by neuron apoptosis due to a traumatic brain injury.

According to an embodiment of the present invention, the phosphodiesterase type 5 inhibitor contained in the composition of the present invention (i) inhibits the formation of degenerative neurons in brain tissues, or (ii) inhibits the expression of caspase-3 or poly ADP ribose polymerase (PARP) in neurons.

According to an embodiment of the present invention, the PDE 5 inhibitor may be administered in a dose of 0.5-2 mg/kg to a subject in need of inhibition of brain neuron apoptosis (see example 1). This administration may be conducted once a day.

In one particular embodiment, the PDE 5 inhibitor may be administered in a dose of 1-2 mg/kg to a subject.

According to an embodiment of the present invention, the composition of the present invention may be administered to a subject 24 to 72 hours after the induction of brain neuron apoptosis.

According to another embodiment of the present invention, the first timing of administration of the composition of the present invention is 24 to 168 hours after the induction of brain neuron apoptosis. In one particular embodiment, the first timing of administration of the composition of the present invention is 24 to 72 hours after the induction of brain neuron apoptosis.

The administration as above can obtain an optimum neuroprotective effect as shown in example 2 below. This administration may be conducted once a day.

According to an embodiment of the present invention, the induction of brain neuron apoptosis may be caused by a brain injury (e.g., ischemic brain injury).

The pharmaceutical composition of the present invention may be administered orally or parenterally.

According to an embodiment of the present invention, the pharmaceutical composition of the present invention may be administered to a subject orally or parentally through a part other than the head. That is, the composition of the present invention can exhibit intended effects of the present invention even when not directly administered to brain tissues, body tissues (e.g., head) covering the brain tissues, and adjacent tissues. In one particular embodiment, the parental administration is subcutaneous administration, intravenous administration, intraperitoneal administration, dermal administration, or intramuscular administration. In another particular embodiment, the parental administration is subcutaneous administration, intravenous administration, or intramuscular administration. In this regard, the blood-brain barrier (BBB) is a unique structure of the central nerve system (CNS) that isolates the brain from the system blood circulation. The BBB prevents the access of many materials (dye, drug, toxin, etc.), which circulate in the blood, to the brain, thereby effectively protecting the brain, but on the other hand, the BBB is a major obstacle in the pharmacological treatment of brain disease. However, as proved in examples below, it was verified that, as a result of performing a histopathological assessment on cerebral tissues after the subcutaneous administration of the PDE 5 inhibitor to a subject through the back, the administration of the PDE 5 inhibitor led to the reduction of cerebral atrophy, reduction of degenerative neurons, the inhibition of expression of capase-3 and PARP, which are apoptosis markers. These results indicate that the PDE 5 inhibitor that is not directly administered to the brain region exhibits a direct pharmaceutical effect on brain cells or tissues, that is, penetrates BBS to have a direct pharmaceutical effect on the brain. These results are surprising in consideration of the well-known knowledge that drugs are generally difficult to penetrate BBS, and thus are difficult to show a direct pharmaceutical effect in the brain tissues.

The pharmaceutically acceptable carrier included in the pharmaceutical composition of the present disclosure may be a commonly used one, including lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable carriers and formulations are described in detail in Remington's Pharmaceutical Sciences (19th ed., 1995).

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

In cases where the phosphodiesterase type 5 inhibitor is orally administered, the composition of the present invention may have a film dosage form. In the present invention, the film may be named a strip, an orally dissolving film, an orally disintegrating film, or the like, and means a dosage form that is stuck inside the mouth, such as, on the tongue, on the oral mucosa, or under the tongue, and then melted. This film dosage form can be taken without water.

In accordance with another aspect of the present invention, there is provided a functional health food for inhibiting brain neuron apoptosis, comprising: (i) a phosphodiesterase type 5 inhibitor; and (ii) a food acceptable food supplement additive.

Since the functional health food of the present invention contains the foregoing PDE 5 inhibitor, descriptions of overlapping contents between the two are omitted to avoid excessive complication of the specification.

The health functional food of the present invention comprises all forms such as functional health foods, nutritional supplements, nutritionals, pharmafoods, health foods, nutraceuticals, designer foods, food additives and feed additives. The types of the foods are not particularly limited, and examples thereof comprise meat, sausage, bread, chocolate, candies, snacks, cookies, pizza, ramen, other noodles, gums, dairy products including ice cream, various soups, beverages, teas, health drinks, alcoholic beverages and vitamin complexes and the like.

The functional health food of the present invention contains, as active ingredients, components that are normally added at the time of food manufacturing, in addition to the PDE 5 inhibitor, and contains, for example, proteins, carbohydrates, fats, nutrients, seasoning, and flavoring agents. Examples of the carbohydrate are monosaccharides, such as glucose and fructose; disaccharides, such as maltose, sucrose, and oligosaccharides; polysaccharides such as dextrin; typical sugars such as cyclodextrin; sugar alcohols, such as, xylitol, sorbitol, and erythritol. Examples of the flavoring agent may be natural flavoring agents (thaumatin, and stevia extract (e.g., rebaudioside A, glycyrrhizin, etc.)) and synthetic flavoring agents (saccharin, aspartame, etc.)

Besides the above, the food of the present invention may contain various nutrients, vitamins, minerals (electrolytes), dietary ingredients, flavoring agents, such as synthetic flavoring agents and natural flavoring agents, a coloring agent, an extender (cheese, chocolate, etc.), pectic acid and its salt, alginic acid and its salt, organic acids, a protective colloid thickener, a PH adjuster, a stabilizer, a preservative, glycerin, alcohol, a carbonating agent used for a carbonated drink, and the like. In consideration of easy accessibility to foods, the food of the present invention is very useful in the inhibition of brain neuron apoptosis and the prevention and treatment of brain nerve disease.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1. Neuroprotective Effects of PDE 5 Inhibiter

Materials and Methods
1. Animals and Husbandry

Total one hundred healthy male Sprague-Dawley (SD) rats (6-wk old upon receipt; Japan; Body weight ranged in 180-200 g upon receipt) were used after acclimatization for 100 days. Animals were allocated five per polycarbonate cage in a temperature (20-25° C.) and humidity (50-55%) controlled room. Light:dark cycle was 12 hr:12 hr, and standard rodent chow (Samyang, Korea) and water were supplied free to access. All animals were treated in accordance with the Guidelines for Care and Use of Laboratory Animals of Daegu Haany University based on the Guide for the Care and Use of Laboratory Animals by Institute of Laboratory Animal Resources, Commission on Life Science, National Research Council, USA on 1996, Washington D.C. Experimental groups were as follows:

TABLE 1

| Experimental groups (Five groups, 10 rats per group were used) | | |
|---|---|---|
| 1 | Sham control | Sham-operated and then, saline as vehicle treated control rats |
| 2 | Neuron apoptosis control (damage-induced group) | Neuron apoptosis-operated and then, saline as vehicle treated control rats |
| 3 | Mirodenafil 0.5 | Neuron apoptosis-operated and then, mirodenafil 0.5 mg/kg treated control rats |
| 4 | Mirodenafil 1 | Neuron apoptosis-operated and then, mirodenafil 1 mg/kg treated control rats |
| 5 | Mirodenafil 2 | Neuron apoptosis-operated and then, mirodenafil 2 mg/kg treated control rats |

2. Preparations and Administration of Test Materials

The mirodenafil (mirodenafil 2HCl; SK Chemical Life Science Business, KR) was used in this experiment. It was white powders and well dissolved in saline. Mirodenafil was stored at 4° C. in a refrigerator to protect from light and humidity until used. Three different dosages, 0.5, 1 and 2 mg/kg of mirodenafil were directly dissolved in saline and subcutaneously administered in a volume of 1 ml/kg on the dorsal back skins, once a day for 28 days from 24 hrs after stabilization periods from operation. In saline and neuron apoptosis control rats, equal volumes of saline as vehicle were administered, instead of mirodenafil, respectively.

3. Preparation of Animal Model for Neuron Apoptosis

The induction of neuron apoptosis was carried out by damaging the right hemisphere of the brain of animals. Specifically, animals were anesthetized with 2 or 3% isoflurane in the mixture of 70% N$_2$O and 28.5% O$_2$, and were maintained with 1 to 1.5% isoflurane in the mixture of 70% N$_2$O and 28.5% O$_2$. After that the temporalis muscle was bisected and reflected through an incision made midway between the eye and the eardrum canal. The proximal MCA was exposed through a subtemporal craniectomy by micro-dental drills without removing the zygomatic arch and without transecting the facial nerve. The artery was then occluded by microbipolar coagulation from just proximal to the olfactory tract to the inferior cerebral vein, and was transected. Mortality was less than 5%. For sham control, all procedures were performed in the same way, with the exception of the occlusion of the MCA.

4. Immunohistochemistry

After deparraffinized of cerebral histological paraffin sections, citrate buffer antigen (epitope) retrieval pretreatment were conducted as previously (Shi S R et al., J Histochem Cytochem. 41:1599-604(1993)). Briefly, pre-heat water bath with staining dish containing 10 mM citrate buffers (pH 6.0) until temperature reaches 95-100° C. Immerse slides in the staining dish and place the lid loosely on the staining dish. Incubate for 20 minutes and turn off the water bath. Place the staining dish at room temperature and allow the slides to cool for 20 minutes. After epitope retrivals, sections were immunostained as following steps:

Incubate sections with methanol and 0.3% H$_2$O$_2$ for 30 minutes for blocking endogenous peroxidase activity at room temperature and rinse in 0.01M phosphate buffered saline (PBS; pH 7.2) for 3 times;

Incubate sections with normal horse serum blocking solution (Vector Lab. Inc., Burlingame, USA. Dilution 1:100) for 1 hour to block non-specific binding of immunoglobulin at room temperature in humidity chamber, and rinse in 0.01M PBS for 3 times;

Incubate sections with primary antisera for overnight at 4° C. in humidity chamber and rinse in 0.01M PBS for 3 times;

Incubate sections with biotinylated universal secondary antibody (Vector Lab., Dilution 1:50) for 1 hour at room temperature in humidity chamber and rinse in 0.01M PBS for 3 times;

Incubate sections with ABC reagents (Vectastain Elite ABC Kit, Vector Lab., Dilution 1:50) for 1 hour at room temperature in humidity chamber and rinse in 0.01M PBS for 3 times;

Incubate sections in Peroxidae substrate kit (Vector Lab.) for 5 min at room temperature and rinse in 0.01M PBS for 3 times;

Counterstain with Mayer's hematoxylin solution and rinse in running tap water for 30 minutes;

Dehydrate through 95% ethanol for 2 minutes, 100% ethanol for 3 times and Clear in xylene for two times; and Coverslip with permanent mounting medium and observed under light microscope (Nikkon, Japan).

Histomorphometry: The nerve cells occupied by over 10% of immunoreactivities, the density, of each antiserum, caspase-3 and PARP were regarded as immunoreactive. In the present study, the numbers of each caspase-3 and PARP-immunoreactive cells among mm$^2$ of ipsilateral peri-infarct/defect cerebral cortex were measured using a computer-assisted image analysis program, respectively.

5. Histopathology

At 29 days after neuron apoptosis rats were sacrificed. Brains were removed, washed in chilled phosphate buffered saline (PBS, pH7.4), and dissected into 6 coronal sections (2 mm thickness) ranging from 2 to 14 mm from the frontal brain pole on the rat brain stainless steel coronal matrix (Harvard, USA). Brain slices prepared by the stainless steel coronal matrix were directly fixed in 10% NBF, not stained with TTC. Then, embedded in paraffin, cross-sectioned, and stained with hematoxylin and eosin (H&E) for observing general histopathology of cerebral cortex. Under H&E stain, the brain atrophic % and the numbers of degenerative neurons (as seen as eosinophilic cells) were calculated as histomorphometry. The histopathologist was blindes to group distribution when this analysis was made.

Histomorphometry: The atrophic % of ipsilateral cerebral cortex was calculated as following equation 1 as compared with intact contralateral hemisphere. In addition, the numbers of degenerative neurons were also measured in the restricted view fields of cerebral cortex, mm$^2$, respectively.

Cerebral atrophy formation=(Contralateral cerebral cortex area−ipsilateral cerebral cortex area)/Contralateral cerebral cortex area×100(%)  [EQUATION 1]

6. Body Weight Measurements

Changes of body weight were measured at 1 day before neuron apoptosis, the day of neuron apoptosis, 1, 7 14, 21, 28 and 29 days after neuron apoptosis using an automatic electronic balance. To reduce the individual differences, the body weight gains after neuron apoptosis and continuous oral treatment of materials were calculated as follows.

Body weight gains (g) during 29 days after neuron apoptosis=(Body weight at the 29 days after neuron apoptosis−body weight at the day of neuron apoptosis)  [EQUATION 2]

7. Sensorimotor Function Assessment—Neurological Motor Behavior Assessment

Sensorimotor function was evaluated by use of limb placing de Ryck M et al., Stroke. 20:1383-90(1989)) and body swing (Borlongan and Sanberg, J Neurosci. 15:5372-8(1995)) tests. These tests were performed one day before neuron apoptosis to obtain a baseline and then at 1, 3, 7, 14, 21 and 28 days after neuron apoptosis. Behavioral tests were done before drug administration on days when both were scheduled. The investigator performing the surgery and behavioral assessments was blinded to treatment assignment.

Limb placing test: Forelimb and hindlimb placement were assessed independently. For the forelimb placing test, the rats were held by their torso with their forepaws hanging free and moved slowly toward the edge of a tabletop, stopping short of touching the vibrissae (for vision-induced placing), touching the vibrissae (for vibrissae-induced placing), making light contact with the front of the forepaw to the edge of the tabletop (for tactile-induced placing), and pressing the forepaws to the edge of the table with increased pressure (for proprioceptive-induced placing). Hindlimb placing was conducted in the same manner as above but with tactile and proprioceptive stimulation applied to the front/top of each hindlimb. Each limb for placing in response to visual, vibrissae, tactile, and proprioceptive stimulation are scored in the following manner (A total of 12 points in forelimb placing test and 6 points in hindlimb placing test means maximal neurological deficit, and 0 points means normal performance):

Normal performance=0 points;
Performance with unilateral limb=1 point;
Performance with a delay (2 seconds) and/or incomplete=2 point;
No performance=3 points.

Body swing tests: Animals were held approximately 2 cm from the base of its tail and elevated to an inch above a surface of a table. A swing was recorded whenever the rat moved its head out of the vertical axis to either side by more than 10° from vertical and then returned to the vertical position. Thirty total swings were counted per animal. After right-hemisphere neuron apoptosis, animals tend to swing to the contralateral (left) side. Thus, the numbers and percentages of body swings to the ipsilateral (right) side were recorded as a measure of recovery, with an intact animal scoring.

8. Cognitive Motor Behavior Assessment

Cognitive testing was conducted using the water tank task (*J Neurosci Methods.* 11:47-60(1984)). 14 and 28 after neuron apoptosis, the rats were given a series of 3 trials, 10 min apart in a large dark-colored tank (150 cm in diameters× 50 cm in height) filled with clear water at a temperature of 22.0±1.0° C. A 15×30 cm submerged platform (2 mm below water surface) was placed in the northwest quadrant of the pool. The release point was always the southern end of the pool. The rats were lowered into the pool facing the wall and were released. The swim paths of the rats for each trials were recorded with a computer interfaced camera tracking system (Smart junior, PanLab, Spain), and the distances (m) and times (sec) taken to reach the escape platform were measured.

9. Statistical Analyse

All data were expressed as mean±standard deviation (S.D.) of ten rats. Multiple comparison tests for different dose groups were conducted. Variance homogeneity was examined using the Levene test (Levene A, *Clin Otalary*, 1981; 6:145-51). If the Levene test indicated no significant deviations from variance homogeneity, the obtain data were analyzed by one way ANOVA test followed by least-significant differences (LSD) multi-comparison test to determine which pairs of group comparison were significantly different. In case of significant deviations from variance homogeneity was observed at Levene test, a non-parametric comparison test, Kruskal-Wallis H test was conducted. When a significant difference is observed in the Kruskal-Wallis H test, the Mann-Whitney U-Wilcoxon Rank Sum W test was conducted to determine the specific pairs of group comparison, which are significantly different. Statistical analyses were conducted using SPSS (Release 14K, SPSS Inc., USA; Ludbrook, *Clin Exp Pharmacol Physiol*, 1997; 24:294-6). In addition, the percent changes between neuron apoptosis control and mirodenafil treated rats were calculated to help the understanding of the efficacy of test material as follow equation 3.

Percentage changes as compared with neuron apoptosis control (%)=[((Data of mirodenafil treated groups−Data of neuron apoptosis control)/Data of neuron apoptosis control)×100]  [EQUATION 3]

Experimental Results

1. Neuron Apoptosis Inhibition Effect of PDE 5 Inhibitor

Figure 1:
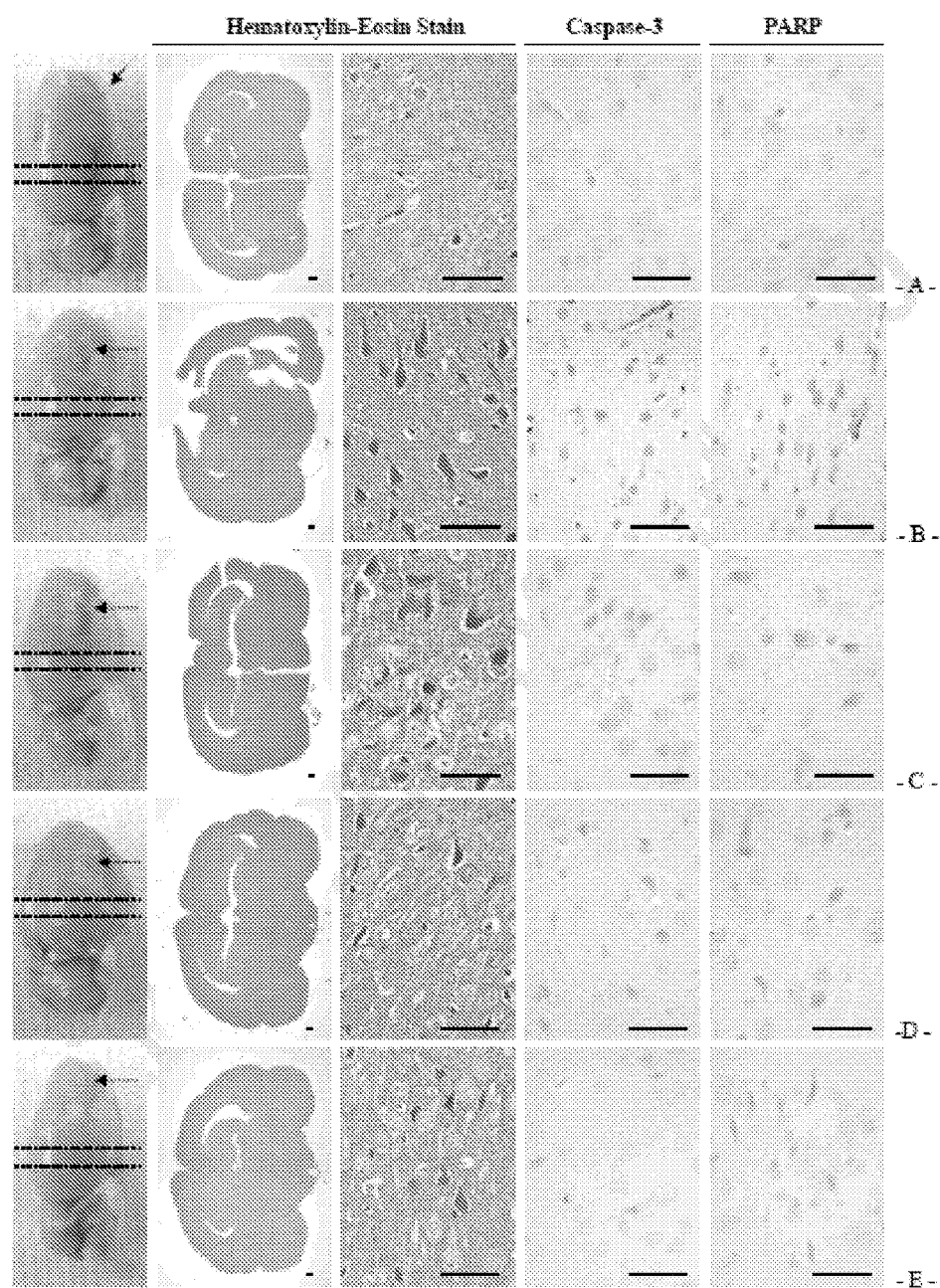
FIG. 1 illustrates histopathological images showing a neuroprotective effect (brain atrophy, degenerative neurons, caspase-3, and PARP) of mirodenafil.
A=Sham control,
B=Neuron apoptosis control,
C=Mirodenafil 0.5 mg/kg treated rats,
D=Mirodenafil 1 mg/kg treated rats,
E=Mirodenafil 2 mg/kg treated rats,
Scale bar=100 μm,
Arrows indicate proximal MCA.

In neuron apoptosis control rats, significant ($p<0.01$) increases atrophic % of ipsilateral cerebral cortex, the numbers of degenerative neurons, caspase-3- and PARP-immunoreactive cells were observed as compared with sham control rats, in the peri-infarct/defect cerebral cortex. However, significant ($p<0.01$) decreases of the numbers of degenerative, caspase-3- and PARP-immunoreactive cells were demonstrated in mirodenafil 0.5 mg/kg treated rats as compared with control. Mirodenafil 1 and 2 mg/kg markedly and significantly ($p<0.01$) inhibited cerebral atrophy and the increases of degenerative, caspase-3- and PARP-immunoreactive cells in the cerebral cortex as compared with control, respectively (Table 2, FIG. 1).

TABLE 2

| Groups | Cerebral atrophic % | Numbers of neurons (cells/mm$^2$ of cerebral cortex) | | |
|---|---|---|---|---|
| | | Degenerative cells | Caspase-3+ | PARP+ |
| Controls | | | | |
| Sham | 2.48 ± 1.79 | 6.10 ± 3.90 | 6.50 ± 3.03 | 7.90 ± 2.13 |
| Neuron apoptosis | 56.27 ± 8.86$^a$ | 81.40 ± 11.15$^a$ | 65.80 ± 12.07$^a$ | 76.10 ± 12.88$^a$ |
| Mirodenafil | | | | |
| 0.5 mg/kg | 51.38 ± 10.74$^a$ | 45.20 ± 8.97$^{ab}$ | 43.80 ± 10.37$^{ab}$ | 47.50 ± 9.44$^{ab}$ |
| 1.0 mg/kg | 30.15 ± 10.28$^{ab}$ | 21.60 ± 9.43$^{ab}$ | 15.50 ± 3.57$^{ab}$ | 17.70 ± 2.00$^{ab}$ |
| 2.0 mg/kg | 26.28 ± 9.12$^{ab}$ | 19.10 ± 2.08$^{ab}$ | 14.50 ± 3.69$^{ab}$ | 16.50 ± 3.81$^{ab}$ |

$^a$ $p < 0.01$ as compared with sham control by MW test
$^b$ $p < 0.01$ as compared with neuron apoptosis control by MW test Specifically, the ipsilateral cerebral atrophic % in mirodenafil 0.5, 1 and 2 mg/kg treated rats were changed as −8.70, −46.42 and −53.31% as compared with neuron apoptosis control rats, respectively.

The numbers of degenerative neurons in mirodenafil 0.5, 1 and 2 mg/kg treated rats were changed as −44.47, −73.46 and −76.54% as compared with neuron apoptosis control rats, respectively.

The numbers of caspase-3-immunoreactive neurons in mirodenafil 0.5, 1 and 2 mg/kg treated rats were changed as −33.43, −76.44 and −77.96% as compared with neuron apoptosis control rats, respectively.

The numbers of PARP-immunoreactive neurons in mirodenafil 0.5, 1 and 2 mg/kg treated rats were changed as −37.58, −76.74 and −78.32% as compared with neuron apoptosis control rats, respectively.

These results demonstrate that PDE5 inhibitors such as mirodenafil can protect neurons by inhibiting neuron apoptosis in brain.

Figure 2:
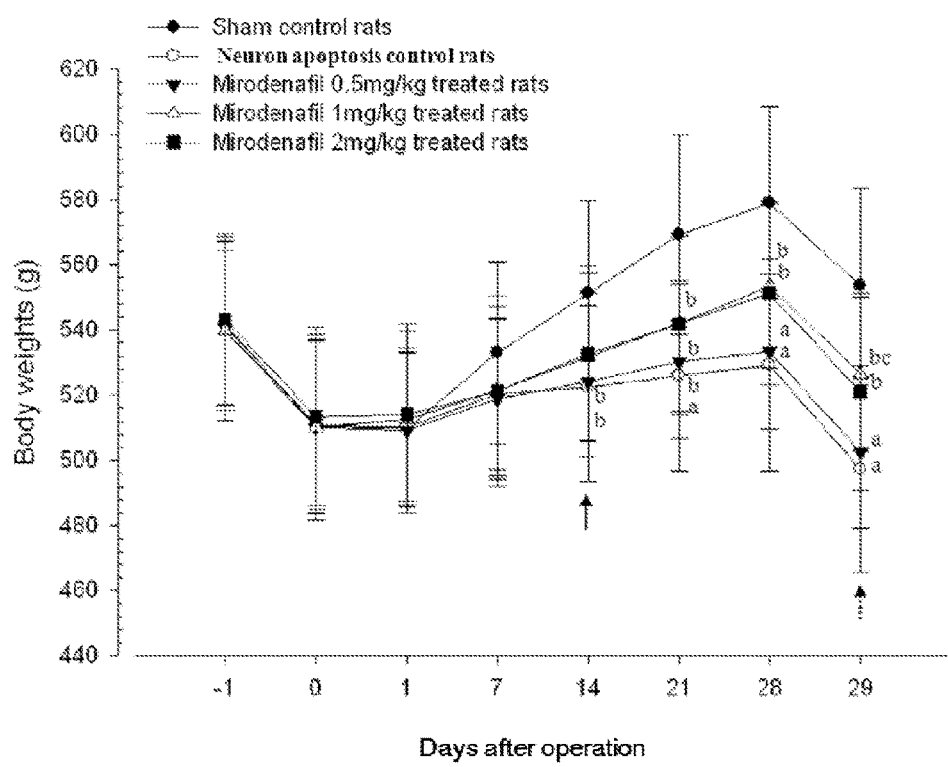
FIG. 2 shows the weight change of an animal model according to the mirodenafil treatment.

2. Neurological and Cognitive Motor Behavior Disorder Ameliorating Effect by PDE 5 Inhibitor Exhibiting Neuroprotective Effect Through Neuron Apoptosis Inhibition (1) Changes on the Body Weights Significant ($p<0.01$ or $p<0.05$) decreases of body weight were detected from 14 days after operation, and consequently, the body weight gains during 29 days of neuron apoptosis were also significantly ($p<0.01$) decreased in neuron apoptosis control rats as compared with sham control rats. Although significant ($p<0.05$) increase of body weight was restricted to 29 days after neuron apoptosis of mirodenafil 1 mg/kg treated rats as compared with neuron apoptosis control rats, but significant ($p<0.01$) increases of body weight gains were detected in mirodenafil 1 and 2 mg/kg treated rats as compared with neuron apoptosis control rats, and marked increase of body weight gains was also demonstrated in mirodenafil 0.5 mg/kg treated rats, respectively (Table 3; FIG. 2). The body weight gains during 29 days of neuron apoptosis in mirodenafil 0.5, 1 and 2 mg/kg treated rats were changed as 45.53, 218.52 and 155.74% as compared with neuron apoptosis control rats, respectively.

Specifically, The forelimb placing test scores in mirodenafil 0.5 mg/kg treated rats were changed as −3.61, −10.34, −12.82, −11.11 and −12.90% at 3, 7, 14, 21 and 28 days after surgery as compared with neuron apoptosis control rats, respectively.

The forelimb placing test scores in mirodenafil 1 mg/kg treated rats were changed as −18.07, −29.89, −32.05, −41.67

TABLE 3

| Groups | Body weights at | | | Weight gains [B − A] |
|---|---|---|---|---|
| | 1 day before surgery | surgery [A] | 29 days after surgery [B] | |
| Controls | | | | |
| Sham | 541.90 ± 26.65 | 510.50 ± 26.76 | 553.40 ± 30.32 | 42.90 ± 13.11 |
| Neuron apoptosis | 541.50 ± 26.08 | 510.90 ± 25.95 | 497.20 ± 31.69$^a$ | −13.70 ± 11.94$^a$ |
| Mirodenafil | | | | |
| 0.5 mg/kg | 540.70 ± 23.66 | 510.20 ± 26.08 | 502.60 ± 23.09$^a$ | −7.60 ± 9.19$^a$ |
| 1.0 mg/kg | 539.70 ± 27.54 | 510.30 ± 28.32 | 526.40 ± 23.45$^{bd}$ | 16.10 ± 7.80$^{ac}$ |
| 2.0 mg/kg | 543.30 ± 26.39 | 513.40 ± 27.21 | 520.90 ± 30.21$^b$ | 7.50 ± 11.20$^{ac}$ |

$^a$p < 0.01 and
$^b$p < 0.05 as compared with sham control by LSD test
$^c$p < 0.01 and
$^d$p < 0.05 as compared with neuron apoptosis control by LSD test (2) Effects on the Sensorimotor Function
<Forelimb Placing Scores>

Significant (p<0.01) increases of forelimb placing test scores were detected from 24 hrs after operation throughout all experimental periods. However, significant (p<0.01) decreases of forelimb placing test scores were detected in mirodenafil 1 and 2 mg/kg treated rats from 3 days after neuron apoptosis as compared with neuron apoptosis control, to sacrifice, respectively. In addition, mirodenafil 0.5 mg/kg treated rats also showed significant (p<0.05) decreases of forelimb placing scores restricted to 14 days after neuron apoptosis as compared with neuron apoptosis control rats in this experiment (Table 4).

and −56.45% at 3, 7, 14, 21 and 28 days after surgery as compared with neuron apoptosis control rats, respectively.

The forelimb placing test scores in mirodenafil 2 mg/kg treated rats were changed as −25.30, −34.48, −39.74, −43.06 and −58.06% at 3, 7, 14, 21 and 28 days after surgery as compared with neuron apoptosis control rats, respectively.

<Hindlimb Placing Scores>

Significant (p<0.01) increases of hindlimb placing test scores were detected from 24 hrs after operation throughout all experimental periods. However, significant (p<0.01 or p<0.05) decreases of hindlimb placing test scores were detected in mirodenafil 1 and 2 mg/kg treated rats from 3

TABLE 4

| Groups | Days after operation | | | | | | |
|---|---|---|---|---|---|---|---|
| | −1 | 1 | 3 | 7 | 14 | 21 | 28 |
| Controls | | | | | | | |
| Sham | 0.70 ± 0.82 | 0.80 ± 0.79 | 0.60 ± 0.52 | 0.80 ± 0.79 | 0.70 ± 0.67 | 0.70 ± 0.67 | 0.80 ± 0.63 |
| Neuron apoptosis | 0.60 ± 0.52 | 12.00 ± 0.00$^d$ | 8.30 ± 1.49$^a$ | 8.70 ± 1.42$^a$ | 7.80 ± 1.03$^a$ | 7.20 ± 0.92$^a$ | 6.20 ± 0.92$^a$ |
| Mirodenafil | | | | | | | |
| 0.5 mg/kg | 0.70 ± 0.67 | 12.00 ± 0.00$^d$ | 8.00 ± 1.15$^a$ | 7.80 ± 1.55$^a$ | 6.80 ± 1.14$^{ac}$ | 6.40 ± 1.17$^a$ | 5.40 ± 1.07$^a$ |
| 1.0 mg/kg | 0.70 ± 0.48 | 12.00 ± 0.00$^d$ | 6.80 ± 1.23$^{ab}$ | 6.10 ± 1.20$^{ab}$ | 5.30 ± 1.06$^{ab}$ | 4.20 ± 1.23$^{ab}$ | 2.70 ± 1.06$^{ab}$ |
| 2.0 mg/kg | 0.60 ± 0.70 | 12.00 ± 0.00$^d$ | 6.20 ± 0.92$^{ab}$ | 5.70 ± 0.67$^{ab}$ | 4.70 ± 0.67$^{ab}$ | 4.10 ± 0.88$^{ab}$ | 2.60 ± 0.84$^{ab}$ |

$^a$p < 0.01 as compared with sham control by LSD test
$^b$p < 0.01 and
$^c$p < 0.05 as compared with neuron apoptosis control by LSD test
$^d$p < 0.01 as compared with sham control by MW test days after neuron apoptosis as compared with neuron apoptosis control, to sacrifice, respectively (Table 5).

detected from 24 hrs after neuron apoptosis operation throughout all experimental periods. However, significant

TABLE 5

| Groups | Days after operation | | | | | | |
|---|---|---|---|---|---|---|---|
| | −1 | 1 | 3 | 7 | 14 | 21 | 28 |
| Controls | | | | | | | |
| Sham | 0.30 ± 0.48 | 0.30 ± 0.48 | 0.30 ± 0.48 | 0.30 ± 0.48 | 0.20 ± 0.42 | 0.20 ± 0.42 | 0.20 ± 0.42 |
| Neuron apoptosis | 0.40 ± 0.52 | 6.00 ± 0.00$^d$ | 4.30 ± 0.67$^a$ | 3.50 ± 0.71$^a$ | 3.10 ± 0.57$^d$ | 3.00 ± 0.67$^a$ | 2.70 ± 0.67$^a$ |
| Mirodenafil | | | | | | | |
| 0.5 mg/kg | 0.50 ± 0.71 | 6.00 ± 0.00$^d$ | 4.00 ± 0.82$^a$ | 3.20 ± 0.79$^a$ | 2.80 ± 0.63$^d$ | 2.60 ± 0.70$^a$ | 2.40 ± 0.97$^a$ |
| 1.0 mg/kg | 0.30 ± 0.48 | 6.00 ± 0.00$^d$ | 3.50 ± 0.71$^{ac}$ | 2.50 ± 0.71$^{ab}$ | 2.10 ± 0.57$^{df}$ | 1.70 ± 0.48$^{ab}$ | 1.10 ± 0.74$^{ab}$ |
| 2.0 mg/kg | 0.40 ± 0.52 | 6.00 ± 0.00$^d$ | 3.30 ± 0.67$^{ab}$ | 2.30 ± 0.82$^{ab}$ | 1.80 ± 1.03$^{de}$ | 1.60 ± 0.84$^{ab}$ | 1.10 ± 0.57$^{ab}$ |

$^a$p < 0.01 as compared with sham control by LSD test
$^b$p < 0.01 and
$^c$p < 0.05 as compared with neuron apoptosis control by LSD test
$^d$p < 0.01 as compared with sham control by MW test
$^e$p < 0.01 and
$^f$p < 0.05 as compared with neuron apoptosis control by MW test Specifically, the hindlimb placing test scores in mirodenafil 0.5 mg/kg treated rats were changed as −6.98, −8.57, −9.68, −13.33 and −11.11% at 3, 7, 14, 21 and 28 days after surgery as compared with neuron apoptosis control rats, respectively.

The hindlimb placing test scores in mirodenafil 1 mg/kg treated rats were changed as −18.80, −28.57, −32.26, −43.33 and −59.26% at 3, 7, 14, 21 and 28 days after surgery as compared with neuron apoptosis control rats, respectively.

The hindlimb placing test scores in mirodenafil 2 mg/kg treated rats were changed as −23.26, −34.29, −41.94, −46.67 and −59.26% at 3, 7, 14, 21 and 28 days after surgery as compared with neuron apoptosis control rats, respectively.

<Body Swings>

Significant (p<0.01) decreases of the numbers and percentages of body swings to the ipsilateral (right) sides were (p<0.01 or p<0.05) increases of ipsilateral body swings were detected from 14 days after neuron apoptosis in mirodenafil 0.5 and 1 mg/kg treated rats, and from 3 days after neuron apoptosis in mirodenafil 2 mg/kg treated rats as compared with neuron apoptosis control, to sacrifice, respectively (Table 6).

TABLE 6

| Groups | Days after operation | | | | | | |
|---|---|---|---|---|---|---|---|
| | −1 | 1 | 3 | 7 | 14 | 21 | 28 |
| [The numbers of body swings to the ipsilateral right sides/total 30 body swings] | | | | | | | |
| Controls | | | | | | | |
| Sham | 14.90 ± 1.20 | 15.10 ± 0.99 | 14.90 ± 1.45 | 15.10 ± 0.74 | 15.50 ± 0.85 | 15.00 ± 1.15 | 15.30 ± 1.25 |
| Neuron apoptosis | 15.00 ± 1.15 | 1.30 ± 1.16$^a$ | 1.80 ± 1.75$^a$ | 2.20 ± 1.32$^a$ | 2.90 ± 1.37$^a$ | 3.60 ± 1.17$^a$ | 4.30 ± 1.25$^a$ |
| Mirodenafil | | | | | | | |
| 0.5 mg/kg | 15.10 ± 0.99 | 1.40 ± 1.17$^a$ | 2.10 ± 1.37$^a$ | 2.40 ± 1.26$^a$ | 4.20 ± 1.62$^{ac}$ | 5.40 ± 1.26$^{ab}$ | 6.20 ± 1.99$^{ac}$ |
| 1.0 mg/kg | 15.10 ± 1.29 | 1.30 ± 0.95$^a$ | 2.70 ± 0.82$^a$ | 3.10 ± 0.88$^a$ | 5.80 ± 1.23$^{ab}$ | 7.30 ± 1.89$^{ab}$ | 11.50 ± 1.58$^{ab}$ |
| 2.0 mg/kg | 15.00 ± 1.15 | 1.20 ± 0.63$^a$ | 3.00 ± 0.82$^{ac}$ | 3.20 ± 0.63$^{ac}$ | 6.00 ± 1.56$^{ab}$ | 8.80 ± 1.23$^{ab}$ | 11.10 ± 1.91$^{ab}$ |
| [The percentages of body swings to the ipsilateral right sides/total 30 body swings] | | | | | | | |
| Controls | | | | | | | |
| Sham | 49.67 ± 3.99 | 50.33 ± 3.31 | 49.67 ± 4.83 | 50.33 ± 2.46 | 51.67 ± 2.83 | 50.00 ± 3.85 | 51.00 ± 4.17 |
| Neuron apoptosis | 50.00 ± 3.85 | 4.33 ± 3.87$^a$ | 6.00 ± 5.84$^a$ | 7.33 ± 4.39$^a$ | 9.67 ± 4.57$^a$ | 12.00 ± 3.91$^a$ | 14.33 ± 4.17$^a$ |
| Mirodenafil | | | | | | | |
| 0.5 mg/kg | 50.33 ± 3.31 | 4.67 ± 3.91$^a$ | 7.00 ± 4.57$^a$ | 8.00 ± 4.22$^a$ | 14.00 ± 5.40$^{ac}$ | 18.00 ± 4.22$^{ab}$ | 20.67 ± 6.63$^{ac}$ |
| 1.0 mg/kg | 50.33 ± 4.29 | 4.33 ± 3.16$^a$ | 9.00 ± 2.74$^a$ | 10.33 ± 2.92$^a$ | 19.33 ± 4.10$^{ab}$ | 24.33 ± 6.30$^{ab}$ | 38.33 ± 5.27$^{ab}$ |
| 2.0 mg/kg | 50.00 ± 3.85 | 4.00 ± 2.11$^a$ | 10.00 ± 2.72$^{ac}$ | 10.67 ± 2.11$^{ac}$ | 20.00 ± 5.21$^{ab}$ | 29.33 ± 4.10$^{ab}$ | 37.00 ± 6.37$^{ab}$ |

$^a$p < 0.01 as compared with sham control by LSD test
$^b$p < 0.01 and
$^c$p < 0.05 as compared with neuron apoptosis control by LSD test Specifically, the numbers and percentages of body swings to ipsilateral right sides in mirodenafil 0.5 mg/kg treated rats were changed as 16.67, 9.09, 44.83, 50.00 and 44.19% at 3, 7, 14, 21 and 28 days after surgery as compared with neuron apoptosis control rats, respectively.

The numbers and percentages of body swings to ipsilateral right sides in mirodenafil 1 mg/kg treated rats were changed as 50.00, 40.91, 100.00, 102.78 and 167.44% at 3, 7, 14, 21 and 28 days after surgery as compared with neuron apoptosis control rats, respectively.

The numbers and percentages of body swings to ipsilateral right sides in mirodenafil 2 mg/kg treated rats were changed as 66.67, 45.45, 106.90, 144.44 and 158.14% at 3, 7, 14, 21 and 28 days after surgery as compared with neuron apoptosis control rats, respectively.

(3) Effects on the Cognitive Motor Behaviors

In sham control, marked decreases of the distances and time to reach the escape platform were noticed with repeated trials, three trials in this study at 14 and 28 days after neuron apoptosis. However, significant ($p<0.01$) increases of the distances and time to reach the escape platform were observed in neuron apoptosis control as compared with sham control, and the reducement with repeated trials were also demonstrated at the both 14 and 28 days after neuron apoptosis in this study. Anyway, mirodenafil 0.5 mg/kg treated rats showed significant ($p<0.01$ or $p<0.05$) deceases of the distance to reach the platform at trial 2 of 14 days after neuron apoptosis and all three trials of 28 days after neuron apoptosis, and the time to reach the platform was also significantly ($p<0.01$ or $p<0.05$) decreases at all measured points except for trial 1 of 14 days after neuron apoptosis. In addition, mirodenafil 1 and 2 mg/kg treated rats also showed significant ($p<0.01$ or $p<0.05$) deceases of the distance and time to reach the platform at all measured points except for trial 1 of 14 days after neuron apoptosis, respectively (Table 7).

TABLE 7

| | At 14 days after cognition/motor function impairment | | | | At 28 days after cognition/motor function impairment |
|---|---|---|---|---|---|
| | Trials | | | | Trials |
| Groups | 1 | 2 | 3 | Mean | 1 |
| The distance to reach the escape platform (m) | | | | | |
| Controls | | | | | |
| Sham | 15.85 ± 1.10 | 10.86 ± 1.46 | 5.93 ± 1.70 | 10.88 ± 1.11 | 10.22 ± 2.32 |
| Neuron apoptosis | 16.21 ± 0.97 | 14.50 ± 1.08$^a$ | 11.95 ± 1.18$^a$ | 14.22 ± 0.82$^a$ | 14.68 ± 1.27$^a$ |
| Mirodenafil | | | | | |
| 0.5 mg/kg | 15.89 ± 1.14 | 13.35 ± 1.02$^{ad}$ | 10.83 ± 0.85$^a$ | 13.36 ± 0.81$^a$ | 13.24 ± 0.83$^{ad}$ |
| 1.0 mg/kg | 15.93 ± 1.21 | 12.89 ± 1.61$^{ac}$ | 9.66 ± 1.42$^{ac}$ | 12.83 ± 1.29$^{ac}$ | 12.65 ± 1.24$^{ac}$ |
| 2.0 mg/kg | 16.18 ± 1.49 | 12.68 ± 0.82$^{ac}$ | 9.52 ± 1.27$^{ac}$ | 12.79 ± 0.64$^{ac}$ | 12.62 ± 1.21$^{ac}$ |
| The time to reach the escape platform (sec) | | | | | |
| Controls | | | | | |
| Sham | 125.0 ± 17.68 | 83.9 ± 17.09 | 59.1 ± 9.95 | 89.3 ± 10.68 | 94.9 ± 13.50 |
| Neuron apoptosis | 148.7 ± 13.33$^a$ | 131.8 ± 11.43$^a$ | 111.6 ± 13.55$^a$ | 130.7 ± 11.70$^a$ | 128.4 ± 10.85$^a$ |
| Mirodenafil | | | | | |
| 0.5 mg/kg | 149.8 ± 11.05$^a$ | 118.0 ± 10.38$^{ad}$ | 91.0 ± 11.49$^{ac}$ | 119.6 ± 9.53$^{ad}$ | 113.7 ± 9.57$^{ac}$ |
| 1.0 mg/kg | 150.9 ± 9.00$^a$ | 115.3 ± 8.19$^{ac}$ | 83.9 ± 10.10$^{ac}$ | 116.7 ± 6.30$^{ac}$ | 106.6 ± 10.52$^{bc}$ |
| 2.0 mg/kg | 151.2 ± 10.59$^a$ | 115.9 ± 12.51$^{ac}$ | 82.7 ± 15.17$^{ac}$ | 116.6 ± 10.88$^{ac}$ | 106.5 ± 9.79$^{bc}$ |

| | At 28 days after cognition/motor function impairment | | |
|---|---|---|---|
| | Trials | | |
| Groups | 2 | 3 | Mean |
| The distance to reach the escape platform (m) | | | |
| Controls | | | |
| Sham | 6.31 ± 1.45 | 4.01 ± 0.91 | 6.85 ± 1.27 |
| Neuron apoptosis | 13.05 ± 1.30$^a$ | 11.75 ± 1.36$^d$ | 13.16 ± 1.25$^a$ |
| Mirodenafil | | | |
| 0.5 mg/kg | 11.22 ± 1.08$^{ad}$ | 9.68 ± 0.75$^{ef}$ | 11.38 ± 0.76$^{ac}$ |
| 1.0 mg/kg | 9.33 ± 2.17$^{ac}$ | 6.19 ± 1.93$^{ef}$ | 9.39 ± 1.33$^{ac}$ |
| 2.0 mg/kg | 9.18 ± 1.46$^{ac}$ | 6.56 ± 1.85$^{ef}$ | 9.46 ± 1.25$^{ac}$ |
| The time to reach the escape platform (sec) | | | |
| Controls | | | |
| Sham | 63.1 ± 10.71 | 44.1 ± 8.67 | 67.3 ± 9.52 |
| Neuron apoptosis | 113.8 ± 9.22$^a$ | 104.6 ± 10.32$^a$ | 115.6 ± 9.43$^a$ |

TABLE 7-continued

| | Mirodenafil | | |
|---|---|---|---|
| 0.5 mg/kg | 88.5 ± 12.48[ac] | 74.1 ± 10.58[ac] | 92.1 ± 9.98[ac] |
| 1.0 mg/kg | 78.4 ± 13.55[ac] | 58.1 ± 9.22[ac] | 81.0 ± 8.68[ac] |
| 2.0 mg/kg | 78.2 ± 8.19[ac] | 57.2 ± 6.43[ac] | 80.6 ± 6.63[ac] |

[a] $p < 0.01$ and
[b] $p < 0.05$ as compared with sham control by LSD test
[c] $p < 0.01$ and
[d] $p < 0.05$ as compared with neuron apoptosis control by LSD test
[e] $p < 0.01$ as compared with sham control by MW test
[f] $p < 0.01$ as compared with sham control by MW test Specifically, the distances to reach the escape platform in water maze tank in mirodenafil 0.5 mg/kg treated rats were changed as −7.93, −9.42, −9.80, −14.02 and −17.56% at trial 2 and 3 of 14 days after neuron apoptosis, trials 1, 2 and 3 of 28 days after surgery as compared with neuron apoptosis control rats, and as −10.47, −18.37, −11.45, −22.23 and −29.16% in time to reach the escape platform, respectively.

The distances to reach the escape platform in water maze tank in mirodenafil 1 mg/kg treated rats were changed as −11.07, −19.20, −13.80, 31 28.51 and −47.33% at trial 2 and 3 of 14 days after neuron apoptosis, trials 1, 2 and 3 of 28 days after surgery as compared with neuron apoptosis control rats, and as −12.52, −24.82, −16.98, −31.11 and −44.46% in time to reach the escape platform, respectively.

The distances to reach the escape platform in water maze tank in mirodenafil 2 mg/kg treated rats were changed as −12.54, −20.37, −14.01, −29.65 and −44.14% at trial 2 and 3 of 14 days after neuron apoptosis, trials 1, 2 and 3 of 28 days after surgery as compared with neuron apoptosis control rats, and as −12.06, −25.90, −17.06, −31.28 and −45.32% in time to reach the escape platform, respectively.

Example 2. Neuroprotective Effect of PDE 5 Inhibitor—Analysis of Timing of Administration Materials and Methods
1. Animals and Husbandry Total one hundred healthy male Sprague-Dawley (SD) rats (6-wk old upon receipt; Japan; Body weight ranged in 170-190 g upon receipt) were used after acclimatization for 16 days. Animals were allocated four per polycarbonate cage in a temperature (20-25° C.) and humidity (50-55%) controlled room. Light:dark cycle was 12 hr:12 hr, and standard rodent chow (Samyang, Korea) and water were supplied free to access. All animals were treated in accordance with the Guidelines for Care and Use of Laboratory Animals of Daegu Haany University based on the Guide for the Care and Use of Laboratory Animals by Institute of Laboratory Animal Resources, Commission on Life Science, National Research Council, USA on 1996, Washington D.C. Experimental groups are as follows:

TABLE 8

| | Experimental groups (Five groups, 8 rats per group were used) | |
|---|---|---|
| 1 | sham control | Sham-operated and then, saline as vehicle treated control rats |
| 2 | Neuron apoptosis control (damage-indeced group) | Neuron apoptosis-operated and then, saline as vehicle treated control rats |
| 3 | Mirodenafil 24 hrs | Mirodenafil 1 mg/kg treated rats from 24 hrs after neuron apoptosis surgery |

TABLE 8-continued

| | Experimental groups (Five groups, 8 rats per group were used) | |
|---|---|---|
| 4 | Mirodenafil 72 hrs | Mirodenafil 1 mg/kg treated rats from 72 hrs after neuron apoptosis surgery |
| 5 | Mirodenafil 168 hrs | Mirodenafil 1 mg/kg treated rats from 168 hrs after neuron apoptosis surgery |

2. Preparations and Administration of Test Materials

The mirodenafil (mirodenafil 2HCl; SK Chemical Life Science Business, KR) was used in this experiment. It was white powders and well dissolved in saline. Mirodenafil was stored at 4° C. in a refrigerator to protect from light and humidity until used. Mirodenafil were directly dissolved in saline as 1 mg/ml concentrations, and subcutaneously administered in a volume of 1 ml/kg on the dorsal back skins from 24, 72 and 168 hrs after neuron apoptosis, once a day for 14 days, respectively. In saline and neuron apoptosis control rats, equal volumes of saline as vehicle were administered, instead of mirodenafil from 24 hrs after neuron apoptosis for 20 days, respectively.

3. Preparation of Animal Model for Neuron Apoptosis

The induction of neuron apoptosis was carried out by damaging the right hemisphere of the brain of animals. Specifically, animals were anesthetized with 2 or 3% isoflurane in the mixture of 70% $N_2O$ and 28.5% $O_2$, and were maintained with 1 to 1.5% isoflurane in the mixture of 70% $N_2O$ and 28.5% $O_2$. After that the temporalis muscle was bisected and reflected through an incision made midway between the eye and the eardrum canal. The proximal MCA was exposed through a subtemporal craniectomy by microdental drills without removing the zygomatic arch and without transecting the facial nerve. The artery was then occluded by microbipolar coagulation from just proximal to the olfactory tract to the inferior cerebral vein, and was transected. Mortality was less than 5%. For sham control, all procedures were performed in the same way, with the exception of the occlusion of the MCA.

4 Immunohistochemistry

After deparaffinized of prepared gastrocnemius muscle histological paraffin sections, citrate buffer antigen (epitope) retrieval pretreatment were conducted as previously (Shi S R et al., *J Histochem Cytochem.* 41:1599-604(1993)). Briefly, pre-heat water bath with staining dish containing 10 mM citrate buffers (pH 6.0) until temperature reaches 95-100° C. Immerse slides in the staining dish and place the lid loosely on the staining dish. Incubate for 20 minutes and turn off the water bath. Place the staining dish at room temperature and allow the slides to cool for 20 minutes. After epitope retrievals, sections were immunostained using avidin-biotin complex (ABC) methods for caspase-3 and PARP. Endogenous peroxidase activity was blocked by incubated in methanol and 0.3% $H_2O_2$ for 30 minutes, and non-specific binding of immunoglobulin was blocked with normal horse serum blocking solution (Vector Lab., Burlingame, Calif., USA. Dilution 1:100) for 1 hr in humidity chamber. Primary antiserum were treated for overnight at 4° C. in humidity chamber, and then incubated with biotinylated universal secondary antibody (Vector Lab., Dilution 1:50) and ABC reagents (Vectastain Elite ABC Kit, Vector Lab., Dilution 1:50) for 1 hr at room temperature in humidity chamber. Finally, reacted with peroxidae substrate kit (Vector Lab.) for 3 min at room temperature. All sections were rinse in 0.01M PBS for 3 times, between steps. The neurons occupied by over 10% of immunoreactivities, the density, of each antiserum for caspase-3 and PARP were regarded as positive, and the mean numbers of caspase-3 and PARPimmunoreactive cells dispersed in the $mm^2$ of ipsilateral peri-infarct/defect cerebral cortex were counted using an automated image analysis process as establish methods (Lee et al., 2010; Song et al., 2012), respectively. The histopathologist was blinded to the group distribution when performing the analysis.

5. Histopathology

At 29 days after neuron apoptosis, rats were sacrificed under deep anesthesia with 3% isoflurane inhalation. Brains were removed, washed in chilled phosphate buffered saline (PBS, pH7.4), and dissected into 6 coronal sections (2 mm thickness) ranging from 2 to 14 mm from the frontal brain pole on the rat brain stainless steel coronal matrix (Harvard, USA). Prepared last 6th cerebral parts were directly fixed in 10% neural buffered formalin. Then, embedded in paraffin, cross-sectioned, and stained with hematoxylin and eosin (H&E) for observing general histopathology of cerebral cortex. Under H&E stain, the brain atrophic % and the numbers of degenerative neurons (as seen as eosinophilic cells) were calculated as histomorphometry. The histopathologist was blindes to group distribution when this analysis was made.

Histomorphometry: The atrophic % of ipsilateral cerebral cortex was calculated as following Equation 4 as compared with intact contralateral hemisphere in prepared peri-infarct/defect histological specimens. In addition, the numbers of degenerative neurons were also measured in the restricted view fields of cerebral cortex, mm2, respectively.

Cerebral atrophy formation=(Contralateral cerebral cortex area−ipsilateral cerebral cortex area)/ Contralateral cerebral cortex area×100(%)  [EQUATION 4]

6. Body Weight Measurements

Changes of body weight were measured at 1 day before neuron apoptosis, the day of neuron apoptosis, 1, 3, 7, 14, 21, 28 and 29 days after neuron apoptosis. To reduce the individual differences, the body weight gains after neuron apoptosis and continuous oral treatment of materials were calculated as follow Equation 5.

Body weight gains (g) during 29 days after neuron apoptosis=(Body weight at the 29 days after neuron apoptosis−body weight at the day of neuron apoptosis)  [EQUATION 5]

7. Sensorimotor Function Assessment—Neurological Motor Behavior Assessment

Sensorimotor function was evaluated by use of limb placing (de Ryck M et al., Stroke. 20:1383-90(1989)) and body swing (Borlongan and Sanberg, *J Neurosci.* 15:5372-8(1995)) tests. These tests were performed at 1 and 28 days after neuron apoptosis. The investigator performing the surgery and behavioral assessments was blinded to treatment assignment.

Limb placing test: Forelimb and hindlimb placement were assessed independently. For the forelimb placing test, the rats were held by their torso with their forepaws hanging free and moved slowly toward the edge of a tabletop, stopping short of touching the vibrissae (for vision-induced placing), touching the vibrissae (for vibrissae-induced placing), making light contact with the front of the forepaw to the edge of the tabletop (for tactile-induced placing), and pressing the forepaws to the edge of the table with increased pressure (for proprioceptive-induced placing). Hindlimb placing was conducted in the same manner as above but with tactile and proprioceptive stimulation applied to the front/top of each hindlimb. Each limb for placing in response to visual, vibrissae, tactile, and proprioceptive stimulation are scored in the following manner: normal performance=0 points; performance with unilateral limb=1 point; performance with a delay (2 seconds) and/or incomplete=2 point; no performance=3 points. A total of 12 points in forelimb placing test and 6 points in hindlimb placing test means maximal neurological deficit, and 0 points means normal performance.

Body swing tests: Animals were held approximately 2 cm from the base of its tail and elevated to an inch above a surface of a table. A swing was recorded whenever the rat moved its head out of the vertical axis to either side by more than 10° from vertical and then returned to the vertical position. Thirty total swings were counted per animal. After right-hemisphere neuron apoptosis, animals tend to swing to the contralateral (left) side. Thus, the numbers and percentages of body swings to the ipsilateral (right) side were recorded as a measure of recovery, with an intact animal scoring.

8. Cognitive Motor Behavior Assessment

Cognitive testing was conducted using the water tank task (*J Neurosci Methods*. 11:47-60(1984)). On the days 14 and 28 after neuron apoptosis, the rats were given a series of 3 trials, 10 min apart in a large dark-colored tank (150 cm in diameters×50 cm in height) filled with clear water at a temperature of 22.0±1.0° C. A 15×30 cm submerged platform (2 mm below water surface) was placed in the northwest quadrant of the pool. The release point was always the southern end of the pool. The rats were lowered into the pool facing the wall and were released. The swim paths of the rats for each trials were recorded with a computer interfaced camera tracking system (Smart junior, PanLab, Spain), and the distances (m) and times (sec) taken to reach the escape platform were measured.

9. Statistical Analyses

All data were expressed as mean±standard deviation (S.D.) of ten rats. Multiple comparison tests for different dose groups were conducted. Variance homogeneity was examined using the Levene test (Levene A, *Clin Otalary,* 1981; 6:145-51). If the Levene test indicated no significant deviations from variance homogeneity, the obtain data were analyzed by one way ANOVA test followed by least-significant differences (LSD) multi-comparison test to determine which pairs of group comparison were significantly different. In case of significant deviations from variance homogeneity was observed at Levene test, a non-parametric comparison test, Kruskal-Wallis H test was conducted. When a significant difference is observed in the Kruskal-Wallis H test, the Mann-Whitney U-Wilcoxon Rank Sum W test was conducted to determine the specific pairs of group comparison, which are significantly different. Statistical analyses were conducted using SPSS for Windows (Release 14K, SPSS Inc., USA; Ludbrook, *Clin Exp Pharmacol Physiol,* 1997; 24:294-6). In addition, the percent changes as compared with neuron apoptosis control and mirodenafil treated rats were calculated to help the understanding of the efficacy of test substances as follow Equation 6 and 7.

Percentage Changes as Compared with Sham Control (%)=[((Data of neuron apoptosis control−Data of sham control rat)/Data of sham control rats)×100]   [EQUATION 6]

Percentage Changes as Compared with neuron apoptosis Control (%)=[((Data of test material treated rats−Data of neuron apoptosis control rats)/Data of neuron apoptosis control rats)×100]   [EQUATION 7]

Experimental Results

1. Neuron Apoptosis Inhibition Effect of PDE 5 Inhibitor

Figure 3:
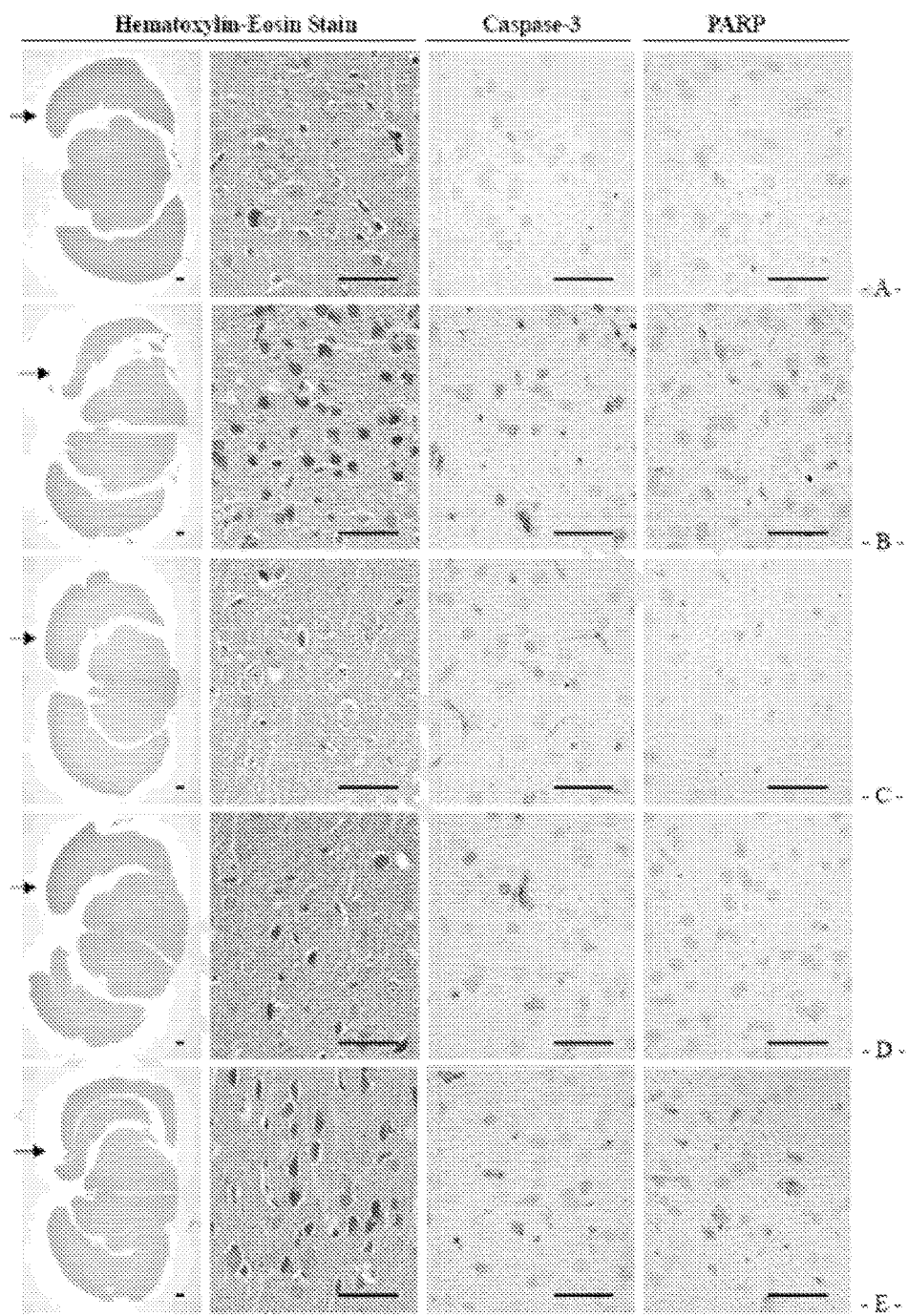
FIG. 3 illustrates histopathological images of brain slices showing a neuroprotective effect (brain atrophy, degenerative neurons, caspase-3, and PARP) of mirodenafil.
A=Sham control,
B=Neuron apoptosis control,
C=Mirodenafil 1 mg/kg treated group from 24 hrs after surgery,
D=Mirodenafil 1 mg/kg treated group from 72 hrs after surgery,
E=Mirodenafil 1 mg/kg treated group from 168 hrs after surgery,
Scale bar=100 μm,
Arrows indicated ipsilateral sides of Neuron apoptosis surgery.

In neuron apoptosis control rats, significant ($p<0.01$) increases atrophic % of ipsilateral cerebral cortex, the numbers of degenerative neurons, caspase-3- and PARP-immunoreactive cells were observed as compared with sham control rats, in the peri-infarct/defect cerebral cortex. However, mirodenafil 1 mg/kg treated rats from 24 and 72 hrs after surgery showed significant ($p<0.01$) decreases of the cerebral atrophy, the number of degenerative, caspase-3- and PARP-immunoreactive cells in the peri-infarct/defect cerebral cortex as compared with neuron apoptosis control rats, respectively. In addition, mirodenafil 1 mg/kg treated rats, initiated from 168 hrs after operation also showed significant ($p<0.05$) decreases of the cerebral atrophy, the number of degenerative, PARP-immunoreactive cells, and non-significant but marked decreases of caspase-3-immunoreactive neurons in the peri-infarct/defect cerebral cortex as compared with neuron apoptosis control rats, respectively (Table 9, FIG. 3).

Specifically, the ipsilateral cerebral atrophic % at 29 days after neuron apoptosis were changed as 1581.66% in neuron apoptosis control rats as compared with sham vehicle control rats, but they were changed as −60.71, −26.37 and −12.31% in mirodenafil 1 mg/kg treated rats from 24, 72 and 168 hrs after surgery as compared with neuron apoptosis control rats, respectively.

The numbers of degenerative neurons in the peri-infarct/defect cerebral cortex at sacrifice were changed as 1625.83% in neuron apoptosis control rats as compared with sham vehicle control rats, but they were changed as −70.64, −45.90 and −15.40% in mirodenafil 1 mg/kg treated rats from 24, 72 and 168 hrs after surgery as compared with neuron apoptosis control rats, respectively.

The numbers of caspase-3-immunoreactive neurons in the peri-infarct/defect cerebral cortex at 29 days after surgery were changed as 1360.00% in neuron apoptosis control rats as compared with sham vehicle control rats, but they were changed as −57.29, −40.63 and −15.57% in mirodenafil 1 mg/kg treated rats from 24, 72 and 168 hrs after surgery as compared with neuron apoptosis control rats, respectively.

The numbers of PARP-immunoreactive neurons in the peri-infarct/defect cerebral cortex at 29 days after surgery were changed as 983.59% in neuron apoptosis control rats as compared with sham vehicle control rats, but they were changed as −53.92, −39.72 and −15.68% in mirodenafil 1 mg/kg treated rats from 24, 72 and 168 hrs after surgery as compared with neuron apoptosis control rats, respectively.

These results demonstrate that PDE5 inhibitors such as mirodenafil can protect neurons by inhibiting neuron apoptosis in brain.

Figure 4:
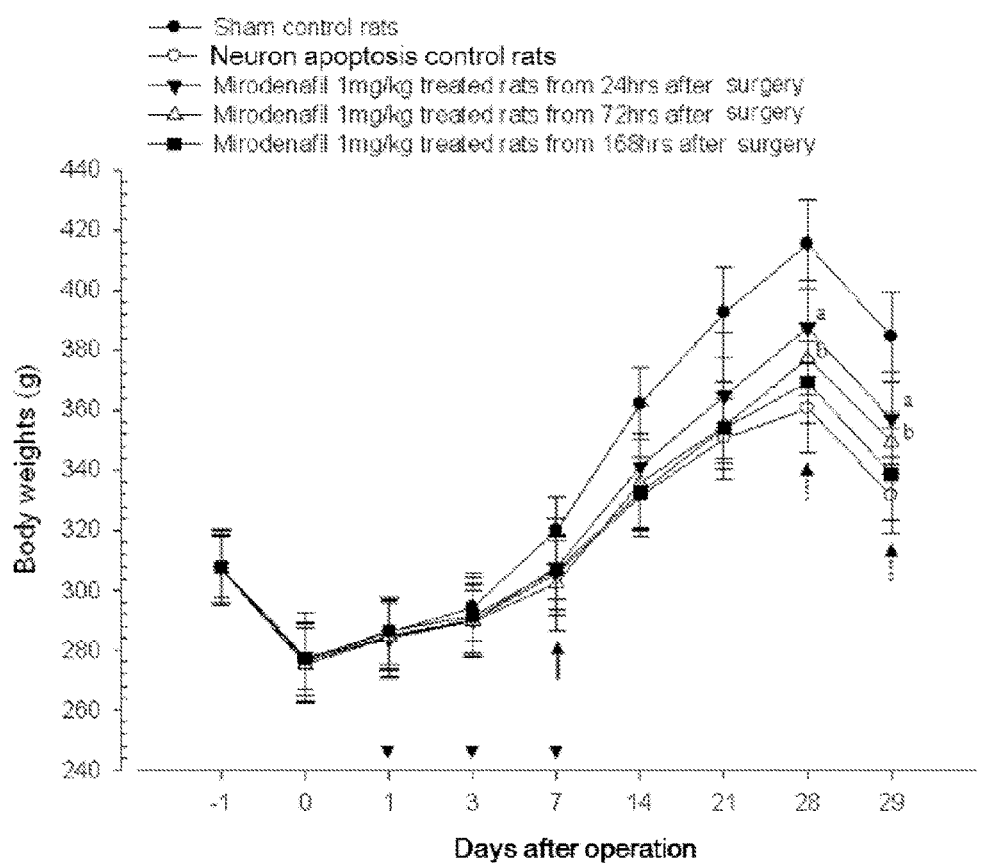
FIG. 4 shows the weight change of an animal model according to the timing of mirodenafil treatment.

2. Neurological and Cognitive Motor Behavior Disorder Ameliorating Effect by PDE 5 Inhibitor Exhibiting Neuroprotective Effect Through Neuron Apoptosis Inhibition (1) Changes on the Body Weights Significant ($p<0.01$ or $p<0.05$) decreases of body weight were detected from 7 days after operation, and consequently, the body weight gains during 29 days of neuron apoptosis were also significantly ($p<0.01$) decreased in neuron apoptosis control rats as compared with sham control rats. Significant ($p<0.01$ or $p<0.05$) increases of body weights were detected at 28 and 29 days after surgery in mirodenafil 1 mg/kg treated rats from 24 and 72 hrs after surgery with significant ($p<0.01$) increases of body weight gains as compared with neuron apoptosis control rats, respectively. Mirodenafil treated rats, initiated 168 hrs after operation did not showed any significant changes on the body weight and gains as compared with neuron apoptosis control rats throughout experimental periods in this study (Table 10; FIG. 4). The body weight gains during 29 days of experimental periods in neuron apoptosis control rats were changed as 48.49% as compared with sham vehicle control rats, but they were changed as 43.24, 33.78 and 11.04% in mirodenafil 1 mg/kg treated rats from 24, 72 and 168 hrs after surgery as compared with neuron apoptosis control rats, respectively.

TABLE 9

| Groups | Cerebral atrophic % | Numbers of neurons cells/mm² of cerebral cortex | | |
|---|---|---|---|---|
| | | Degenerative cells | Caspase-3+ | PARP+ |
| Controls | | | | |
| Sham | 3.31 ± 1.76 | 4.50 ± 2.15 | 4.81 ± 1.87 | 7.24 ± 1.78 |
| Neuron apoptosis | 55.72 ± 5.90$^a$ | 77.66 ± 10.00$^a$ | 70.26 ± 10.98$^a$ | 78.43 ± 9.04$^a$ |
| Start time of mirodenafil 1 mg/kg (after operation) | | | | |
| 24 hrs | 21.90 ± 3.13$^{ab}$ | 22.80 ± 3.69$^{ab}$ | 30.01 ± 4.90$^{ab}$ | 36.14 ± 5.32$^{ab}$ |
| 72 hrs | 41.03 ± 5.05$^{ab}$ | 42.01 ± 6.14$^{ab}$ | 41.71 ± 6.34$^{ab}$ | 47.28 ± 5.36$^{ab}$ |
| 168 hrs | 48.87 ± 3.25$^{ac}$ | 65.70 ± 7.64$^{ac}$ | 59.33 ± 5.13$^a$ | 66.13 ± 9.61$^{ac}$ |

Values are expressed as Mean ± SD of eight rat brain specimens
$^a$$p < 0.01$ as compared with sham control by MW test
$^b$$p < 0.01$ and
$^c$$p < 0.05$ as compared with neuron apoptosis control by MW test

TABLE 10

| Groups | Body weights at | | | Weight gains [B − A] |
|---|---|---|---|---|
| | Before surgery | surgery [A] | 29 days after surgery [B] | |
| Controls | | | | |
| Sham | 307.00 ± 10.88 | 276.75 ± 11.97 | 384.50 ± 15.18 | 107.75 ± 9.04 |
| Neuron apoptosis | 307.63 ± 12.27 | 276.13 ± 13.14 | 331.63 ± 12.53$^a$ | 55.50 ± 4.78$^a$ |
| Start time of mirodenafil 1 mg/kg (after operation) | | | | |
| 24 hrs | 307.75 ± 15.84 | 277.63 ± 15.07 | 357.13 ± 15.38$^{ab}$ | 79.50 ± 14.09$^{ab}$ |
| 72 hrs | 307.25 ± 11.36 | 275.13 ± 12.21 | 349.38 ± 10.28$^{ac}$ | 74.25 ± 14.95$^{ab}$ |
| 168 hrs | 307.88 ± 10.53 | 277.00 ± 10.41 | 338.63 ± 15.26$^a$ | 61.63 ± 6.78$^a$ |

Values are expressed as Mean ± SD of eight rats, g
$^a$p < 0.01 as compared with sham control by LSD test
$^b$p < 0.01 and
$^c$p < 0.05 as compared with neuron apoptosis control by LSD test (2) Effects on the Sensorimotor Function <Forelimb Placing Scores>

Figure 5:
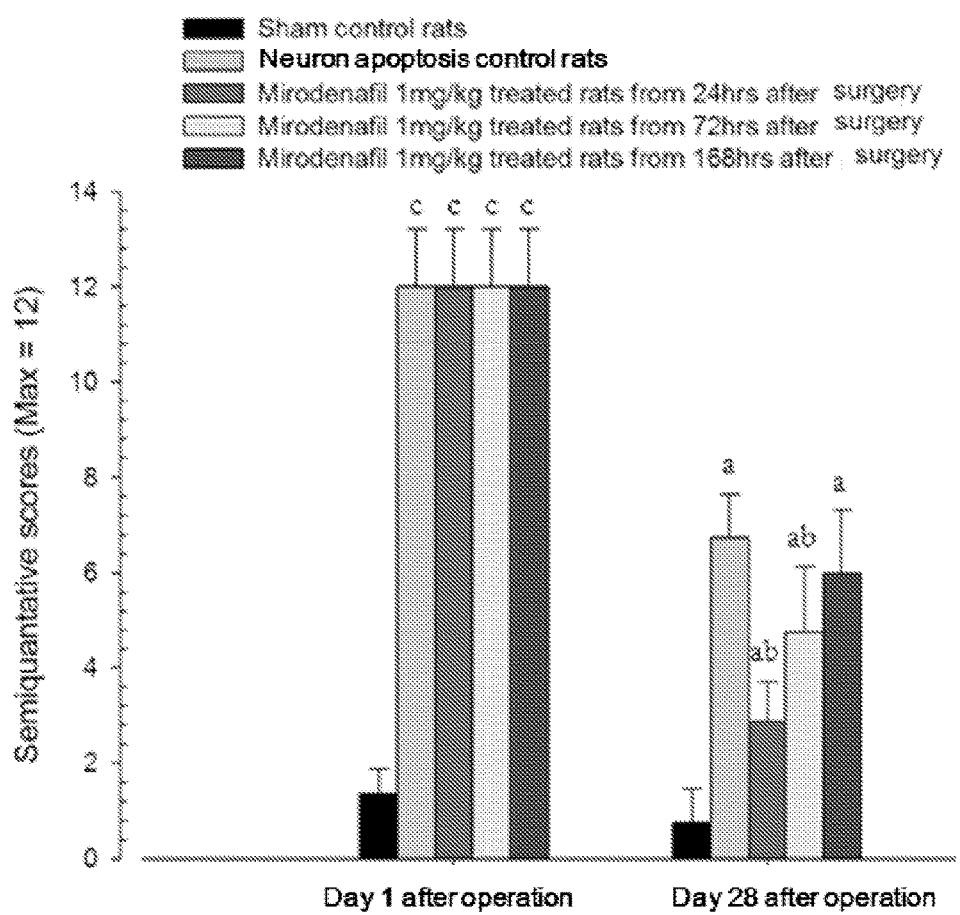
FIG. 5 shows the change in the forelimb placing test score according to the timing of mirodenafil treatment.

Rats showing the max forelimb score (score 12) were selected at 24 hrs after neuron apoptosis and started administration in this study. Significant (p<0.01) increases of forelimb placing test scores were detected at 28 days after operation in neuron apoptosis control rats as compared with sham control rats. Significant (p<0.01) decreases of forelimb placing test scores were detected in mirodenafil 1 mg/kg treated rats, initiated 24 and 72 hrs after surgery as compared with neuron apoptosis control, at 1 day before sacrifice, respectively. But mirodenafil 1 mg/kg treated rats from 168 hrs after surgery did not showed significant changes on the forelimb placing scores as compared with neuron apoptosis control rats in this experiment (FIG. 5).

Specifically, the forelimb placing test scores at 28 days after neuron apoptosis were changed as 800.00% in neuron apoptosis control rats as compared with sham vehicle control rats, but they were changed as −57.41, −29.63 and −11.11% in mirodenafil 1 mg/kg treated rats from 24, 72 and 168 hrs after surgery as compared with neuron apoptosis control rats, respectively.

<Hindlimb Placing Scores>

Rats showing the max hindlimb score (score 6) were selected at 24 hrs after neuron apoptosis and started administration in this study. Significant (p<0.01) increases of hindlimb placing test scores were detected at 28 days after surgery in neuron apoptosis control rats as compared with sham control rats. Significant (p<0.01) decreases of hindlimb placing test scores were detected in mirode nafil 1 mg/kg treated rats, initiated 24 and 72 hrs after surgery as compared with neuron apoptosis control, respectively. No significant changes on the hindlimb placing test scores were detected in mirodenafil 1 mg/kg treated rats from 168 hrs after surgery as compared with neuron apoptosis control rats in this experiment (FIG. 6).

Specifically, the hindlimb placing test scores at 28 days after neuron apoptosis were changed as 1050.00% in neuron apoptosis control rats as compared with sham vehicle control rats, but they were changed as −65.22, −39.13 and −17.39% in mirodenafil 1 mg/kg treated rats from 24, 72 and 168 hrs after surgery as compared with neuron apoptosis control rats, respectively.

<Body Swings>

Rats with similar decreases of body swings to the ipsilateral operated right sides (1-4 swings; 3.33-13.33%) were selected at 24 hrs after neuron apoptosis and started administration in this study. Significant (p<0.01) decreases of the numbers and percentages of body swings to the ipsilateral (right) sides were detected at 28 days after operation in neuron apoptosis control rats as compared with sham control rats. Significant (p<0.01) increases of ipsilateral body swings were detected in mirodenafil 1 mg/kg treated rats from 24 and 72 hrs after surgery as compared with neuron apoptosis control rats, at 1 day before sacrifice, respectively. But mirodenafil 1 mg/kg treated rats from 168 hrs after surgery did not showed significant changes on the numbers and percentages of body swings to the ipsilateral right sides as compared with neuron apoptosis control rats in the present study (FIG. 7).

Specifically, the numbers and percentages of body swings to ipsilateral right sides at 28 days after neuron apoptosis were changed as −59.35% in neuron apoptosis control rats as compared with sham vehicle control rats, but they were changed as 82.00, 48.00 and 14.00% in mirodenafil 1 mg/kg treated rats from 24, 72 and 168 hrs after surgery as compared with neuron apoptosis control rats, respectively.

(3) Effects on the Cognitive Motor Behaviors—Water Maze Test

Sham control rats showed marked decreases of the distances and time to reach the escape platform with repeated trials, three trials in this study at 28 days after neuron apoptosis. However, significant (p<0.01) increases of the distances and time to reach the escape platform were observed in neuron apoptosis control as compared with sham control, and the reducement with repeated trials were also noticeably decreased at 28 days after neuron apoptosis in this study. Mirodenafil 1 mg/kg treated rats, initiated from 24 and 72 hrs after surgery showed significant (p<0.01 or p<0.05) deceases of the distance to reach the platform at all measured points, trial 1, 2 and 3 with mean values of 28 days after neuron apoptosis. Mirodenafil 1 mg/kg treated rats did not showed any significant changes on the distance and time to reach the platform at all measured points in this study (FIG. 8).

Specifically, the mean distances to reach the escape platform in water maze tank at 28 days after neuron apoptosis were changed as 85.74% in neuron apoptosis control rats as compared with sham vehicle control rats, but they were changed as −26.45, −16.05 and −6.42% in mirodenafil 1 mg/kg treated rats from 24, 72 and 168 hrs after surgery as compared with neuron apoptosis control rats, respectively.

The mean time to reach the escape platform in water maze tank at 28 days after neuron apoptosis were changed as 79.67% in neuron apoptosis control rats as compared with sham vehicle control rats, but they were changed as −24.49, −17.33 and −5.36% in mirodenafil 1 mg/kg treated rats from 24, 72 and 168 hrs after surgery as compared with neuron apoptosis control rats, respectively.

3. Discussion

Marked decreases of body weights, disorders of sensorimortor functions—increases of fore and hindlimb placing test scores, decreases of the numbers and percentages of body swings to the ipsilateral (right) sides, of cognitive motor behaviors—increases of the distances and time to reach the escape platform including the inhibition of the decreases with repeated trials were observed with focal cerebral defects. In addition, marked increases of the atrophy, numbers of degenerative, caspase-3- and PARP-immunoreactive cells around peri-infarct/defect ipsilateral cerebral cortex were also observed in neuron apoptosis control as compared with sham control rats, respectively.

These brain damage related damages around peri-infarct/defect cerebral cortex, disorders of sensorimortor functions and cognitive motor behaviors were markedly inhibited by treatment of mirodenafil 1 mg/kg, initiated from 24 and 72 hrs after neuron apoptosis surgery for 14 days. Treatment of mirodenafil 1 mg/kg from 168 hrs after surgery also showed effective inhibitory effects on the damages around peri-infarct/defect cerebral cortex and neuron apoptosis. It, therefore, the optimal dosing regimen of mirodenafil, the initial treatment time on the cognition and motor function recovery from ischemic brain damage is considered as 24-72 hrs after surgery.

As progress of ischemic brain damages, marked disordered of cognition and sensorimotor functions were induce, and consequently significant body weight decreases are followed (Garcia et al., 1986; Schöller et al., 2004; Wang et al., 2012). And also, significant (p<0.01 or p<0.05) decreases of body weights were detected in all animal groups subjected to the neuron apotosis surgery from 7 days after surgery as compared with sham control in the present study, and body weight gains during 29 days of experimental periods were also significantly (p<0.01) decreased. Although significant (p<0.01 or p<0.05) increase of body weight was restricted to 28 and 29 days after neuron apotosis of mirodenafil 1 mg/kg treated rats, initiated from 24 and 72 hrs after surgery as compared with neuron apoptosis control rats, but no significant effects on the body weight and gains were detected in mirodenafil 1 mg/kg treated rats from 168 hrs after operation as compared with neuron apotosis control rats, respectively. These finding on the body weights were considered as direct evidences that treatment of mirodenafil 1 mg/kg should be initiated within 24-72 hrs after brain damages to show favorable inhibition effects on the body weight decreases from the disorders of cognition and sensorimotor functions.

limb placing test is one of representative sensorimotor function test, in which abnormal placing of fore and hindlimbs were respectively scored and higher scores mean higher disorders of sensorimotor functions. In addition, body swing test is also frequently used sensorimotor function test; normal animals showed about 5:5 (50%) of body swings to the left and right sides but the frequency and percentages of body swings to the damaged ipsilateral sides were dramatically decreased in ischemic brain damaged rodents (Roof et al., 2001; Menniti et al., 2009). Water maze test is one of selectable cognitive behavioral test, in which the distances and tome to reach the escape platforms in water filled tank were dramatically increased in a animal has cognitive disorders, especially the reducement with repeated trials were also inhibited as cognitive disorders.

In the present study, although mirodenafil 1 mg/kg, initiated from 24 and 72 hrs after surgery markedly and time-dependently inhibited the disorders of sensorimotor functions and cognitive motor behaviors in all limb placing, body swing and water maze tests as compared with neuron apoptosis control, but mirodenafil 1 mg/kg treated rats from 168 hrs after surgery did not showed any significant favorable changes on the sensorimotor functions and cognitive motor behaviors, as direct evidences that treatment of mirodenafil 1 mg/kg should be initiated within 24-72 hrs after neuron apoptosis to show favorable accelerations of the recovery of sensorimotor function and cognitive motor behavioral disorders, In the present study, marked increases of ipsilateral cerebral cortex atrophy around pri-infarct/defect regions were detected in neuron apoptosis control as compared with sham control, but mirodenafil 1 mg/kg, initiated from 24, 72 and 168 hrs after neuron apoptosis surgery, significantly decreased the cerebral atrophic changes as compared with neuron apoptosis control, and also markedly decreased the numbers of degenerative neurons in cerebral cortex.

Caspase-3 and PARP are one of key executioners of apoptosis (Nunez et al., 1998; Barrett et al., 2001), the increase of caspase-3 and PARP-immunoreactive cells in the cerebral cortex represents their apoptosis and related damages. As a result of the experimentation, caspase-3 and PARP-immunoreactive neurons were decreased by treatment of all three different doing regimen of mirodenafil 1 mg/kg applied in this study. Therefore, in cases of administration from 24-168 hours after brain injury, the PDE 5 inhibitor was observed to exhibit a certain extent of neuroprotective effect around the brain injury, but the neuroprotective effect was observed to be lowered as the timing of administration onset is delayed.

Having described a preferred embodiment of the present invention, it is to be understood that variants and modifications thereof falling within the spirit of the invention may become apparent to those skilled in this art, and the scope of this invention is to be determined by appended claims and their equivalents.

The invention claimed is:

1. A method for inhibiting brain neuron apoptosis in a subject in need thereof, comprising administering a composition containing a phosphodiesterase type 5 inhibitor selected from the group consisting of udenafil, dasantafil, or avanafilin in an effective amount to the subject.

2. The method of claim 1, wherein the subject is a patient with brain nerve disease.

3. The method of claim 1, wherein the brain nerve disease is selected from the group consisting of neuronal degenerative disease, ischemic stroke, cognitive dysfunction, and motor dysfunction.

4. The method of claim 1, wherein the neuronal degenerative disease is selected from the group consisting of dementia, Huntington's disease, Parkinson's disease, and amyotrophic lateral sclerosis.

5. The method of claim 1, wherein the cognitive dysfunction is memory loss, learning disability, agnosia, amnesia, aphasia, apraxia, or delirium.

6. The method of claim 1, wherein the motor dysfunction is motor disturbance, paralysis, ataxia, dyskinesia, spasticity, or dystonia.

7. The method of claim 1, wherein the phosphodiesterase type 5 inhibitor inhibits the formation of degenerative neurons in brain tissues or inhibits the expression of caspase-3 or poly ADP ribose polymerase (PARP) in neurons.

8. The method of claim 1, wherein the composition is administered to a human orally or parentally through a part other than the head.

9. The method of claim 1, wherein the composition is a film dosage form when the phosphodiesterase type 5 inhibitor is orally administered.

* * * * *

UNITED STATES PATENT AND TRADEMARK OFFICE
CERTIFICATE OF CORRECTION

PATENT NO. : 10,064,865 B2  
APPLICATION NO. : 15/663092  
DATED : September 4, 2018  
INVENTOR(S) : Myung Hwa Kim et al.

Page 1 of 1

It is certified that error appears in the above-identified patent and that said Letters Patent is hereby corrected as shown below:

In the Claims

Column 28:
Claim 3, Line 52, "The method of claim 1," should read --The method of claim 2--;

Claim 4, Line 56, "The method of claim 1," should read --The method of claim 3--;

Claim 5, Line 60, "The method of claim 1," should read --The method of claim 3--; and Claim 6, Line 63, "The method of claim 1," should read --The method of claim 3--.

Signed and Sealed this
Eighteenth Day of November, 2025

John A. Squires
*Director of the United States Patent and Trademark Office*